(12) United States Patent
Eilertsen

(10) Patent No.: US 8,987,220 B2
(45) Date of Patent: Mar. 24, 2015

(54) PRODUCTION OF REPROGRAMMED CELLS WITH RESTORED POTENTIAL

(75) Inventor: Kenneth J. Eilertsen, Baton Rouge, LA (US)

(73) Assignee: Nupotential, Inc., Baton Rouge, LA (US)

( * ) Notice: Subject to any disclaimer, the term of this patent is extended or adjusted under 35 U.S.C. 154(b) by 0 days.

(21) Appl. No.: 12/573,539

(22) Filed: Oct. 5, 2009

(65) Prior Publication Data

US 2010/0159459 A1    Jun. 24, 2010

Related U.S. Application Data

(62) Division of application No. 11/497,064, filed on Aug. 1, 2006, now Pat. No. 7,601,699.

(60) Provisional application No. 60/704,465, filed on Aug. 1, 2005.

(51) Int. Cl.
*A61K 48/00* (2006.01)
*C07H 21/02* (2006.01)
*C07H 21/04* (2006.01)
*C12N 15/85* (2006.01)
*C12Q 1/70* (2006.01)
*C12N 15/113* (2010.01)

(52) U.S. Cl.
CPC ........ *C12N 15/1137* (2013.01); *C12N 2310/14* (2013.01)
USPC ............... 514/44; 536/23.1; 536/24.5; 435/6; 435/325

(58) Field of Classification Search
None
See application file for complete search history.

(56) References Cited

U.S. PATENT DOCUMENTS 7,601,699 B2 * 10/2009 Eilertsen ..................... 514/44 R

* cited by examiner

*Primary Examiner* — Amy Bowman
(74) *Attorney, Agent, or Firm* — Whyte Hirschboeck Dudek S.C.

(57) ABSTRACT

A method for treating cells and/or nuclear transfer units and/or stem cells in culture with such compounds, individually or in combinations, is described. The method results in a globally hypomethylated genome and a restoration of cell differentiation and/or developmental potential, or potentiality. In addition, a method for the in vitro production of reprogrammed cells which have had differentiation potential (totipotential, pluripotential, or multipotential) restored by demethylating the genome is described.

9 Claims, 8 Drawing Sheets

SEQUENCE LISTING

<160> NUMBER OF SEQ ID NOS: 43

<210> SEQ ID NO 1
<211> LENGTH: 22
<212> TYPE: DNA
<213> ORGANISM: Artificial
<220> FEATURE:
<223> OTHER INFORMATION: Human siRNA to DNMT1
<220> FEATURE:
<221> NAME/KEY: modified_base
<222> LOCATION: (6)..(6)
<223> OTHER INFORMATION: "n" at position 6 is uridine (u)
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: modified_base
<222> LOCATION: (15)..(16)
<223> OTHER INFORMATION: "n" at positions 15 and 16 are uridine (u)
<220> FEATURE:
<221> NAME/KEY: misc_feature
<222> LOCATION: (15)..(16)
<223> OTHER INFORMATION: n is a, c, g, or t
<220> FEATURE:
<221> NAME/KEY: modified_base
<222> LOCATION: (18)..(18)
<223> OTHER INFORMATION: "n" at position 18 is uridine (u)
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: modified_base
<222> LOCATION: (21)..(21)
<223> OTHER INFORMATION: "n" at position 21 is deoxythymidine (dT)
<220> FEATURE:
<221> NAME/KEY: misc_feature
<222> LOCATION: (21)..(22)
<223> OTHER INFORMATION: n is a, c, g, or t
<220> FEATURE:
<221> NAME/KEY: modified_base
<222> LOCATION: (22)..(22)
<223> OTHER INFORMATION: "n" at position 21 is deoxythymidine (dT)

<400> SEQUENCE: 1
aagcangagc accgnncncc nn                                              22

<210> SEQ ID NO 2
<211> LENGTH: 19
<212> TYPE: RNA
<213> ORGANISM: Artificial
<220> FEATURE:
<223> OTHER INFORMATION: Murine siRNA to Dnmt3b

<400> SEQUENCE: 2
gcaaugaucu cucuaacgu                                                  19

<210> SEQ ID NO 3
<211> LENGTH: 19
<212> TYPE: RNA
<213> ORGANISM: Artificial
<220> FEATURE:
<223> OTHER INFORMATION: Murine siRNA to Dnmt3b

<400> SEQUENCE: 3
ggaaugcgcu ggguacagu                                                  19

<210> SEQ ID NO 4
<211> LENGTH: 19
<212> TYPE: RNA
<213> ORGANISM: Artificial

```
<220> FEATURE:
<223> OTHER INFORMATION: Murine siRNA to Dnmt3b

<400> SEQUENCE: 4
uaaucuggcu accuucaau                                                  19

<210> SEQ ID NO 5
<211> LENGTH: 19
<212> TYPE: RNA
<213> ORGANISM: Artificial
<220> FEATURE:
<223> OTHER INFORMATION: Murine siRNA to Dnmt3b

<400> SEQUENCE: 5
gcaaagguuu auaugaggg                                                  19

<210> SEQ ID NO 6
<211> LENGTH: 19
<212> TYPE: RNA
<213> ORGANISM: Artificial
<220> FEATURE:
<223> OTHER INFORMATION: Human siRNA to Dnmt1

<400> SEQUENCE: 6
ggaagaagag uuacuauaa                                                  19

<210> SEQ ID NO 7
<211> LENGTH: 19
<212> TYPE: RNA
<213> ORGANISM: Artificial
<220> FEATURE:
<223> OTHER INFORMATION: Human siRNA to Dnmt1

<400> SEQUENCE: 7
gagcggaggu gucccaaua                                                  19

<210> SEQ ID NO 8
<211> LENGTH: 19
<212> TYPE: RNA
<213> ORGANISM: Artificial
<220> FEATURE:
<223> OTHER INFORMATION: Human siRNA to Dnmt1

<400> SEQUENCE: 8
ggacgacccu gaccucaaa                                                  19

<210> SEQ ID NO 9
<211> LENGTH: 19
<212> TYPE: RNA
<213> ORGANISM: Artificial
<220> FEATURE:
<223> OTHER INFORMATION: Human siRNA to Dnmt1

<400> SEQUENCE: 9
gaacggugcu caugcuuac                                                  19

<210> SEQ ID NO 10
<211> LENGTH: 19
<212> TYPE: RNA
<213> ORGANISM: Artificial
<220> FEATURE:
<223> OTHER INFORMATION: Human siRNA to Dnmt3a

<400> SEQUENCE: 10
gcacaagggu accuacggg                                                  19
```

```
<210> SEQ ID NO 11
<211> LENGTH: 19
<212> TYPE: RNA
<213> ORGANISM: Artificial
<220> FEATURE:
<223> OTHER INFORMATION: Human siRNA to Dnmt3a

<400> SEQUENCE: 11
caagagagcg gcuggugua                                                    19

<210> SEQ ID NO 12
<211> LENGTH: 19
<212> TYPE: RNA
<213> ORGANISM: Artificial
<220> FEATURE:
<223> OTHER INFORMATION: Human siRNA to Dnmt3a

<400> SEQUENCE: 12
gcacugaaau ggaaagggu                                                    19

<210> SEQ ID NO 13
<211> LENGTH: 19
<212> TYPE: RNA
<213> ORGANISM: Artificial
<220> FEATURE:
<223> OTHER INFORMATION: Human siRNA to Dnmt3a

<400> SEQUENCE: 13
gaacugcuuu cuggagugu                                                    19

<210> SEQ ID NO 14
<211> LENGTH: 19
<212> TYPE: RNA
<213> ORGANISM: Artificial
<220> FEATURE:
<223> OTHER INFORMATION: Human siRNA to Dnmt3b

<400> SEQUENCE: 14
gaaaguacgu cgcuucuga                                                    19

<210> SEQ ID NO 15
<211> LENGTH: 19
<212> TYPE: RNA
<213> ORGANISM: Artificial
<220> FEATURE:
<223> OTHER INFORMATION: Human siRNA to Dnmt3b

<400> SEQUENCE: 15
acaaauggcu ucagauguu                                                    19

<210> SEQ ID NO 16
<211> LENGTH: 19
<212> TYPE: RNA
<213> ORGANISM: Artificial
<220> FEATURE:
<223> OTHER INFORMATION: Human siRNA to Dnmt3b

<400> SEQUENCE: 16
gcucuuaccu uaccaucga                                                    19

<210> SEQ ID NO 17
<211> LENGTH: 19
<212> TYPE: RNA
<213> ORGANISM: Artificial
<220> FEATURE:
<223> OTHER INFORMATION: Human siRNA to Dnmt3b
```

-continued

```
<400> SEQUENCE: 17
uuuaccaccu gcugaauua                                                    19

<210> SEQ ID NO 18
<211> LENGTH: 19
<212> TYPE: RNA
<213> ORGANISM: Artificial
<220> FEATURE:
<223> OTHER INFORMATION: Murine siRNA to Dnmt1

<400> SEQUENCE: 18
ggaaagagau ggcuuaaca                                                    19

<210> SEQ ID NO 19
<211> LENGTH: 19
<212> TYPE: RNA
<213> ORGANISM: Artificial
<220> FEATURE:
<223> OTHER INFORMATION: Murine siRNA to Dnmt1

<400> SEQUENCE: 19
gcugggagau ggcgucaua                                                    19

<210> SEQ ID NO 20
<211> LENGTH: 19
<212> TYPE: RNA
<213> ORGANISM: Artificial
<220> FEATURE:
<223> OTHER INFORMATION: Murine siRNA to Dnmt1

<400> SEQUENCE: 20
gauaagaaac gcagaguug                                                    19

<210> SEQ ID NO 21
<211> LENGTH: 19
<212> TYPE: RNA
<213> ORGANISM: Artificial
<220> FEATURE:
<223> OTHER INFORMATION: Murine siRNA to Dnmt1

<400> SEQUENCE: 21
gguagagagu uacgacgaa                                                    19

<210> SEQ ID NO 22
<211> LENGTH: 19
<212> TYPE: RNA
<213> ORGANISM: Artificial
<220> FEATURE:
<223> OTHER INFORMATION: Murine siRNA to Dnmt3a

<400> SEQUENCE: 22
cgcgauuucu ugagucuaa                                                    19

<210> SEQ ID NO 23
<211> LENGTH: 19
<212> TYPE: RNA
<213> ORGANISM: Artificial
<220> FEATURE:
<223> OTHER INFORMATION: Murine siRNA to Dnmt3a

<400> SEQUENCE: 23
cgaauugugu cuuggugga                                                    19

<210> SEQ ID NO 24
```

```
-continued

<211> LENGTH: 19
<212> TYPE: RNA
<213> ORGANISM: Artificial
<220> FEATURE:
<223> OTHER INFORMATION: Murine siRNA to Dnmt3a

<400> SEQUENCE: 24
aaacaucgag gacauuugu                                               19

<210> SEQ ID NO 25
<211> LENGTH: 19
<212> TYPE: RNA
<213> ORGANISM: Artificial
<220> FEATURE:
<223> OTHER INFORMATION: Murine siRNA to Dnmt3a

<400> SEQUENCE: 25
caagggacuu uaugagggu                                               19

<210> SEQ ID NO 26
<211> LENGTH: 19
<212> TYPE: RNA
<213> ORGANISM: Artificial
<220> FEATURE:
<223> OTHER INFORMATION: Human siRNA to MTHFR

<400> SEQUENCE: 26
agugagagcu ccaaagaua                                               19

<210> SEQ ID NO 27
<211> LENGTH: 19
<212> TYPE: RNA
<213> ORGANISM: Artificial
<220> FEATURE:
<223> OTHER INFORMATION: Human siRNA to MTHFR

<400> SEQUENCE: 27
gaagugaguu uggugacua                                               19

<210> SEQ ID NO 28
<211> LENGTH: 19
<212> TYPE: RNA
<213> ORGANISM: Artificial
<220> FEATURE:
<223> OTHER INFORMATION: Human siRNA to MTHFR

<400> SEQUENCE: 28
gaccaaagag uuacaucua                                               19

<210> SEQ ID NO 29
<211> LENGTH: 19
<212> TYPE: RNA
<213> ORGANISM: Artificial
<220> FEATURE:
<223> OTHER INFORMATION: Human siRNA to MTHFR

<400> SEQUENCE: 29
gcaagugucu uugaagucu                                               19

<210> SEQ ID NO 30
<211> LENGTH: 19
<212> TYPE: RNA
<213> ORGANISM: Artificial
<220> FEATURE:
<223> OTHER INFORMATION: Human siRNA to Cbs

<400> SEQUENCE: 30
```

-continued agacggagca gacaaccua                              19

<210> SEQ ID NO 31
<211> LENGTH: 19
<212> TYPE: RNA
<213> ORGANISM: Artificial
<220> FEATURE:
<223> OTHER INFORMATION: Human siRNA to Cbs

<400> SEQUENCE: 31
caccaccgcu gaugagauc                              19

<210> SEQ ID NO 32
<211> LENGTH: 19
<212> TYPE: RNA
<213> ORGANISM: Artificial
<220> FEATURE:
<223> OTHER INFORMATION: Human siRNA to Cbs

<400> SEQUENCE: 32
ggacgguggu ggacaagug                              19

<210> SEQ ID NO 33
<211> LENGTH: 19
<212> TYPE: RNA
<213> ORGANISM: Artificial
<220> FEATURE:
<223> OTHER INFORMATION: Human siRNA to Cbs

<400> SEQUENCE: 33
ggaagaaguu cggccugaa                              19

<210> SEQ ID NO 34
<211> LENGTH: 19
<212> TYPE: RNA
<213> ORGANISM: Artificial
<220> FEATURE:
<223> OTHER INFORMATION: Murine siRNA to MTHFR

<400> SEQUENCE: 34
cgccauggcu acagaguaa                              19

<210> SEQ ID NO 35
<211> LENGTH: 19
<212> TYPE: RNA
<213> ORGANISM: Artificial
<220> FEATURE:
<223> OTHER INFORMATION: Murine siRNA to MTHFR

<400> SEQUENCE: 35
gcggaaacca gccugauga                              19

<210> SEQ ID NO 36
<211> LENGTH: 19
<212> TYPE: RNA
<213> ORGANISM: Artificial
<220> FEATURE:
<223> OTHER INFORMATION: Murine siRNA to MTHFR

<400> SEQUENCE: 36
cagaaggccu accucgaau                              19

<210> SEQ ID NO 37
<211> LENGTH: 19
<212> TYPE: RNA

-continued

<213> ORGANISM: Artificial
<220> FEATURE:
<223> OTHER INFORMATION: Murine siRNA to MTHFR

<400> SEQUENCE: 37
cauacgagcu gcggqucaa                                              19

<210> SEQ ID NO 38
<211> LENGTH: 19
<212> TYPE: RNA
<213> ORGANISM: Artificial
<220> FEATURE:
<223> OTHER INFORMATION: Murine siRNA to Cbs

<400> SEQUENCE: 38
gcaaacagcc uaugaggug                                              19

<210> SEQ ID NO 39
<211> LENGTH: 19
<212> TYPE: RNA
<213> ORGANISM: Artificial
<220> FEATURE:
<223> OTHER INFORMATION: Murine siRNA to Cbs

<400> SEQUENCE: 39
gcaaaguccu cuacaagca                                              19

<210> SEQ ID NO 40
<211> LENGTH: 19
<212> TYPE: RNA
<213> ORGANISM: Artificial
<220> FEATURE:
<223> OTHER INFORMATION: Murine siRNA to Cbs

<400> SEQUENCE: 40
gaucgaagau gcugagcga                                              19

<210> SEQ ID NO 41
<211> LENGTH: 18
<212> TYPE: RNA
<213> ORGANISM: Artificial
<220> FEATURE:
<223> OTHER INFORMATION: Murine siRNA to Cbs

<400> SEQUENCE: 41
caacccuuug gcacacua                                               18

<210> SEQ ID NO 42
<211> LENGTH: 16
<212> TYPE: DNA
<213> ORGANISM: Artificial
<220> FEATURE:
<223> OTHER INFORMATION: PCR primer for 5' upstream region of human GNMT

<400> SEQUENCE: 42
ggggtaccag catctt                                                 16

<210> SEQ ID NO 43
<211> LENGTH: 27
<212> TYPE: DNA
<213> ORGANISM: Artificial

```
<220> FEATURE:
<223> OTHER INFORMATION: PCR primer for 5' upstream region of human GNMT

<400> SEQUENCE: 43
gcgagatctc ctgcgccgcg cctggct                                       27
```

PRODUCTION OF REPROGRAMMED CELLS WITH RESTORED POTENTIAL

CROSS-REFERENCE TO RELATED APPLICATIONS

This application is a divisional application of U.S. patent application Ser. No. 11/497,064 filed Aug. 1, 2006, which claims benefit of provisional U.S. patent application Ser. No. 60/704,465 filed Aug. 1, 2005. The contents of these applications are hereby incorporated by reference in their entirety herein.

FIELD OF THE INVENTION

This invention relates generally to the fields of cell biology, stem cells, cell differentiation, somatic cell nuclear transfer and cell-based therapeutics. More specifically, this invention is directed to methods and products for cell reprogramming and cell-based therapeutics. Methods of isolation and culture, as well as therapeutic uses for the isolated cells are also provided.

DESCRIPTION OF THE PRIOR ART

Recent dietary studies have described an interaction between methyl donor status, single-carbon metabolism and DNA methylation [1-12]. DNA methylation is associated with developmental status and differentiation potential [13-19]. Moreover, a clear requirement for somatic cell nuclear transfer (SCNT)-induced reprogramming and reprogramming associated with normal fertilization is DNA demethylation [20]. It is within this context that the following background material is reviewed.

During development of multicellular organisms, different cells and tissues acquire different programs of gene expression. These distinct gene expression patterns appear to be substantially regulated by epigenetic modifications such as DNA methylation, histone modifications and various chromatin-binding proteins [21, 22]. Thus each cell type within a multicellular organism has a unique epigenetic signature which is thought to become "fixed" once cells differentiate or exit the cell cycle.

However, some cells undergo major epigenetic "reprogramming" during normal development or certain disease situations. Reprogramming involves the removal of epigenetic marks in the nucleus, followed by establishment of a different set of marks [23-25]. For example, at fertilization, gametic epigenetic marks are erased and replaced with embryonic marks required for totipotency and embryonic development. Reprogramming also occurs in primordial germ cells where parental imprints are erased to restore totipotency. Cancer cells and cells that transdifferentiate also are thought to undergo reprogramming. Finally, dramatic reprogramming is required following SCNT for the purposes of reproductive cloning and stem cell therapy [26-33].

Recently, new insights have been obtained into epigenetic reprogramming in normal development and SCNT. Although insights into the mechanisms of reprogramming and the factors involved are still rudimentary, the foundational knowledge is now reaching a stage at which more detailed concepts can be developed and novel experimental approaches can be devised to examine mechanistic aspects that will provide novel commercial opportunities. A brief summary of in vivo-induced (fertilization and embryogenesis) and in vitro-induced SCNT reprogramming follows.

Epigenetic Reprogramming and Development

In Vivo Reprogramming—Fertilization

DNA Methylation: In mice, at fertilization, the parental genomes are in different stages of the cell cycle with distinct epigenetic marks and chromatin organization. The paternal genome delivered by the mature sperm is single copy and is packaged densely with protamines. The maternal genome is arrested at metaphase II and its two-copy genome is packaged with histones. At fertilization, the protamines are replaced with histones and the maternal genome completes meiosis. After histone acquisition, the paternal genome undergoes a genome-wide loss of DNA methylation as detected by indirect immunofluorescence [34] and bisulphite sequencing [35]. Demethylation is completed before DNA replication begins in the paternal pronucleus. It should be noted, however, that not all regions of the genome are demethylated at this stage. It is believed that the oocyte cytoplasm contains demethylation factors that specifically target or exclude certain sequence classes in sperm chromatin.

Histone Modification: Maternal chromatin is organized so that DNA methylation and chromatin modifications are abundant at fertilization. These include both nucleohistone modifications and chromatin proteins associated with active and repressive states. For example, histone modifications typically associated with an active state, such as acetylated lysine and H3K4me are found in the female pronucleus [34, 36, 37]. Heterochromatic modifications such as H3K9me2/3, H3K27me1 and H41C20me3, largely associated with a repressive chromatin state, are also present.

Histones associated with the male pronucleus are highly acetylated [34, 36]; however, immediately upon histone incorporation, H3K4me1, H3K9me1 and H3K27me1 are detectable [37-39]. This occurs when DNA methylation is still present in the male pronucleus. The progressive histone modifications occurring to the paternal genome presumably lead to a chromatin state equivalent to that of the maternal genome.

Preimplantation Development

Passive demethylation: From the one cell to blastocyst stage in the mouse, there are further changes in global DNA methylation. DNA methylation is reduced progressively with each cleavage division and this loss is dependent on DNA replication [40, 41]. Dnmt1o, a DNMT1 protein inherited from the oocyte, is excluded during the first three cleavage divisions [42, 43], accounting for the loss of methylation by a passive mechanism.

Histone modification: The degree to which histone modifications are reprogrammed during passive DNA demethylation is unclear at present.

Epigenetic Asymmetry and Lineage Commitment

Methylation: The first lineage allocation event in mammalian embryogenesis occurs at the morula stage and results in the formation of the Inner Cell Mass (ICM) and trophoectoderm (TE) lineages in the blastocyst. The mechanism for the cell fate decision is unknown. Interestingly, two-cell blastomeres are still totipotent but by the four-cell stage (in mice) lineage bias is present based on decreased totipotential [44]. Global differences in DNA methylation between extraembryonic and embryonic lineages have been detected and the differences are detectable as early as the blastocyst stage at which combinations of active and passive demethylation have resulted in a lower state of methylation in the TE. In contrast, the ICM has an increased level of global methylation due to de novo methylation likely caused by DNMT3b, a de novo DNA methyltransferase, which is detectable in blastocyst ICM, but not TE [34].

Histone modification: In mice, histone H3K9me3 marks heterochromatic foci in the ICM and H3K27me1, met and me3 are more abundant in the ICM than the TE [38]. The inactive X chromosome and certain imprinted regions are marked in the TE by H327me and H3K9me. In general, as with DNA methylation, higher levels of specific repressive histone methylation marks also are found in the ICM when compared to TE. Thus epigenetic asymmetry is required for development.

Somatic Cell Nuclear Transfer: One method of altering epigenetic marks experimentally is by SCNT or cloning. SCNT requires that a differentiated somatic cell nucleus be reprogrammed to a state of totipotency in an oocyte environment in which nuclear DNA material has been removed (often referred to as "enucleation"). All epigenetic marks that have been examined in cloned embryos and adults from multiple species show abnormalities and most SCNT embryos also differ from each other in the precise epigenetic profile they possess, indicating that SCNT-induced epigenetic reprogramming is a haphazard and stochastic process [30-33, 45].

In addition, development of SCNT embryos is highly variable with the vast majority dying at all stages of development, and the survivors having a variety of abnormalities. Of those that develop to later gestation stages or to term, many have placental abnormalities and a significant proportion die perinatally from poor adaptation to extrauterine life. Because offspring of cloned animals appear normal, most developmental problems of clones likely are caused by epigenetic defects. Both the development and the epigenetic abnormalities of SCNT embryos tend to be more severe the earlier they are examined, with less abnormal ones surviving to later stages [46].

Epigenetic defects described in cloned offspring and SCNT embryos include errors in X-inactivation [47, 48], imprinting [49-51], DNA methylation (both global and specific loci) [36, 47, 52, 53], histone acetylation [43], methylation [43] and alterations in gene expression [54] including the failure to reactivate Oct4, a key pluripotency and developmentally important gene [55-57].

Reprogramming induced by SCNT therefore appears to have at least two important requirements: removal of nuclear proteins and demethylation of somatic cell DNA, the latter apparently being the most important. For example, Somonsson & Gurdon observed considerable delay of Oct4 expression when methylated somatic nuclei from mouse thymus cells were injected into *Xenopus oocytes* [20]. The delay declined when the nuclei were deproteinized prior to nuclear transfer. However when unmethylated DNA, e.g., bacterial plasmid, was injected, there was no detectable delay. This indicates that when all repressive proteins have been removed from nuclei, a substantial delay still occurs and that DNA must be demethylated before transcription can ensue. In addition, using a hypomorphic allele of Dnmt1, Blelloch et al demonstrated demethylation of somatic donor cells improved cloning efficiency and production of embryonic stem cells in vitro indicating restoration of differentiation and developmental potential of a differentiated cell is enabled by reduced DNA methylation [136].

Mechanisms for Removal of Methylation from DNA Not Understood: The removal of methylation from DNA (or histones for that matter) is not understood mechanistically. The loss of DNA methylation of the paternal genome in the zygote is likely to be an enzyme-catalyzed, active demethylation. An oocyte also can actively demethylate a transferred somatic nucleus, suggesting the activity is present. Several candidate biochemical pathways have been suggested that would either remove the methyl group in the C5 position of the cytidine ring directly (direct demethylation) or the cytidine base (indirect demethylation). To date, direct methods to remove the methyl group have either not been described or have not been validated.

Indirect pathways to demethylation involve DNA repair: For example, DNA glycosylases such as thymidine DNA glycosylase and methyl-binding domain protein 4 normally repair T:G mismatches thought to result from spontaneous deamination of 5 meC. More recently it has been shown that activation-induced cytidine deaminase and Apobec1, cytidine deaminases, can deaminate 5 meC to result in T and that these enzymes are expressed in oocytes and germ cells. This activity of cytidine deaminases coupled with base excision repair theoretically could result in demethylation without DNA replication, but would still require extensive base excision repair in the early zygote.

Environmental Factors: A growing body of evidence suggests modifiable environmental factors such as diet can influence DNA methylation. For example, prenatal feeding of a methyl-supplemented diet can increase the level of DNA methylation and phenotypic expression of genes in offspring. The coat color in mice is determined by agouti gene expression. This is determined by the DNA methylation status of the long terminal repeat of the agouti gene in the hair follicle. If this region is hypermethylated, the mouse is agouti in color, whereas if the mouse is hypomethylated the mouse is yellow. When pregnant female mice were fed a methyl-supplemented diet enriched in zinc, methionine, betaine, choline, folate, and vitamin $B_{12}$, there was an alteration in the methylation status of the agouti long terminal repeat and none of the pups had a yellow coat [58]. Thus, in utero exposure to nutrients can lead to epigenetic modifications of the genome in the offspring.

Folate's Role in DNA Methylation: Folate, a water soluble B-vitamin, plays a significant and modulatory role in DNA methylation status. The sole biochemical function of folate is mediating the transfer of one-carbon moieties [59-61] and thus has a central role in one-carbon metabolism. Animal studies have further shown that folate deficiency causes genomic and gene specific hypomethylation in rat liver and the degree appears to depend on the severity and duration of folate depletion [62, 63]. DNA hypomethylation also has been identified in lymphocytes of humans on low dietary folate and can be reversed by folate repletion [64]. The effect of folate deficiency with respect to DNA methylation, however, is also highly complex. For example, folate deficiency with or without reductions in DNMT1, did not affect overall genomic DNA methylation levels or the methylation levels of two candidate genes E-cadherin and p53, in normal or neoplastic tissue.

One-Carbon Metabolism

The Importance of SAM:SAH Ratios and Nutrient Role in Regulating DNA Methylation: The availability of nutrients can play an important role in regulating DNA methylation. Moreover, factors involved in one-carbon metabolism also likely play an important role in methylation status because they influence the supply of methyl groups and therefore the biochemical pathways of methylation processes. Methyl groups supplied from the diet, in the form of choline and methionine, or from the folate-dependent one-carbon pool, must be activated to S-adenosylmethionine (SAM) to serve as substrates in transmethylation reactions. Because S-adenosylhomocysteine (SAH) is a product of transmethylation reactions and a potent inhibitor of SAM-dependent methyltransferases, the ratio of SAM:SAH is an important index of transmethylation potential [65, 66]. When the ratio is high, methylation potential is high. When the ratio is low, methylation potential is low. It is well known that folate depletion alone is a sufficient perturbing force to diminish SAM pools. This leads to an increase in cellular levels of SAH because the equilibrium of the SAH-homocysteine interconversion actually favors SAH synthesis. Therefore when homocysteine metabolism is inhibited, as in folate deficiency, cellular SAH levels will be increased. Increased SAH inhibits methyltransferases activity and consequently DNA methylation reactions.

Glycine-N-methyltransferase (GNMT) Optimizes Transmethylation Reactions: The cytosolic enzyme GNMT functions to optimize transmethylation reactions by regulating the SAM:SAH ratio. When methyl groups are abundant and SAM levels are elevated, GNMT disposes of the excess methyl groups by forming sarcosine from glycine. SAM also reduces the supply of methyl groups originating from the one-carbon pool by inhibiting 5,10-methylenetetrahydrofolate reductase (MTHFR) [67, 68], the enzyme responsible for the synthesis of 5-methyletrahydrofolate (5-methyl-THF). 5-Methyl-THF is folate coenzyme that donates its methyl group to homocysteine to form methionine. Because 5-methyl-THF also binds to GNMT and inhibits its activity [69, 70], a decrease in 5-methyl-THF levels due to inhibition of MTHFR by SAM results in an increase in the activity of GNMT. Factors that activate GNMT lead to downregulation of methyltransferases, including DNA methyltransferases.

To date, there have been no reports testing the hypothesis that activation of GNMT in cells in culture results in reduced DNA methylation. However, a few reports have described dietary manipulation of GNMT in rodents [71-73]. For example, diets supplemented with vitamin A and vitamin A derivatives, e.g. all-trans retinoic acid (ATRA), result in increased GNMT activity and hypomethylated DNA in rat hepatocytes, while decreases in dietary folate, choline, betaine and vitamins $B_{6 \& 12}$ also result in decreased DNA methylation in specific tissues. Thus, manipulations of methionine cycle components and adjusting the nutrient availability of methyl donors represent possible in vitro approaches to demethylate DNA and restore potential. To date, no prior attempts to reprogram or alter the efficiency of reprogramming by modifying components involved in single-carbon metabolism, altering nutrient availability, and/or altering GNMT have been reported.

Current Methods for Inducing Cell Reprogramming: Current methods for inducing cell reprogramming in mammals depend primarily upon SCNT, involving nuclear reprogramming and to a lesser extent exposure to cell extracts, fusion of cell types and removal of nuclear proteins. None of these methods, however, overcome the primary rate-limiting step of reducing DNA methylation levels required for efficient reprogramming.

Nuclear Reprogramming Inefficient: Nuclear reprogramming is dependent on chromatin state and specifically demethylation of DNA, which is typically inefficient or slow. As an example, SCNT cloning requires efficient reprogramming of gene expression to silence donor cell gene expression and activate an embryonic pattern of gene expression. Recent observations indicate that reprogramming may be initiated by early events that occur soon after SCNT, but then continues as development progresses through cleavage and probably gastrulation. Because reprogramming is slow and progressive, NT units have dramatically altered characteristics as compared to fertilized embryos.

The methods described above for nuclear transfer are generally known to the industry, and have been or are being applied to applications for directing differentiation of stem cells. However, nearly all of the applications depend upon nuclear transfer technologies. Geron (Menlo Park Calif.) has used embryonic stem cells to produce nerve cells and heart muscle cells and has made advances in manipulating stem cells to produce other kinds of tissue. Infigen, Inc. (DeForest, Wis.) also received several nuclear transfer patents primarily directed to livestock cloning applications.

In other attempts to improve efficiency of nuclear transfer, Dr. Rudolph Jaenisch of MIT, Whitehead Institute uses cDNA microarrays to establish the molecular criteria for nuclear reprogramming specifically in nuclear transfer. Dr. Jaenisch's primary focus is on human disease such as cancer, and reprogramming cancers, and designing strategies to improve epigenetic reprogramming. H is main efforts have been focused on understanding the mechanisms that establish DNA methylation and reprogramming the methylated genome. Dr. Jaenisch is attempting to develop a nuclear transfer-generated unit devoid of methylation by knocking out DNMT1 in donor cell lines and using the lines to produce NT units [136].

Dr. Keith Latham of Temple University is examining how inefficient reprogramming affects cloned embryos. Dr. Latham's research focuses primarily on physiologic data—examining changes in phenotypes after cloning [137, 139].

Dr. Kevin Eggan, of Harvard University is assessing how the developmental fate of an adult cell can be restored (reprogrammed), using nuclear transfer as a model, and made headlines in 2005 by fusing a human skin cell with an embryonic stem cell to create a hybrid that looked and acted like the stem cell, potentially laying a foundation for creating tailor-made, genetically matched stem cells for patients [138].

Among other methods under investigation for production of stem cells or stem-like cells are the practices of Uri Verlinsky, of the Reproductive Genetics Institute (In Vitro Fertilization Clinic, Chicago, Ill.). Verlinsky employs a method that uses a cell fusion process for fusing somatic cells with stem cells, on the theory that the molecules of the somatic cells will direct the differentiation of the stem cells into the same type of cell as the somatic cell. Verlinsky has reportedly produced 10 embryonic stem cell lines using his new StemBrid (stem/hybrid) technique. No embryos are used.

SUMMARY OF THE INVENTION

An object of the present invention is directed to a process for restoring cell differentiation potential by reducing global DNA methylation of the cell.

A further object of the present invention is directed to the treatment of cells and/or nuclear transfer (NT) units and/or stem cells in culture to yield a globally hypomethylated genome and restored potential of the cell for differentiation (e.g., pluripotential, multipotential, and/or totipotential), defined as the cell's ability to differentiate into new cell types.

The present invention is directed to a method for reprogramming a eukaryotic cell. The method comprises, as step (a), decreasing S-adenosylmethione-to-S-adenosylhomocysteine ratio (SAM-to-SAH ratio) in the eukaryotic cell. The SAM-to-SAH ratio can be decreased to 0.1 or less, preferably 0.5 or less, and most preferably 1.00 or less. Step (a) can include contacting the cell with a siRNA selected from the group consisting of SEQ. ID. NOS: 1-41. Further, step (a) can include increasing expression, activity, or both expression and activity of glycine-N-methyl transferase within the eukaryotic cell. Step (a) can also include contacting the cell with an amount of a retinoic acid effective to increase expression, activity, or both expression and activity of glycine-N-methyl transferase within the cell. In addition, the method includes, as step (b), reducing levels of 5-methylcytosine in DNA within the eukaryotic cell. It is within the scope of the present invention to perform steps (a) and (b) simultaneously. Step (b) also includes specifically suppressing expression, activity, or expression and activity of DNA methyltransferases within the eukaryotic cell. Step (b) can also comprise contacting the cell with a DNA methyltransferase inhibitor. Further, step (b) can comprise contacting the cell with a suppression-effective amount of a small-interfering ribonucleic acid (siRNA) dimensioned and configured to suppress expression of DNA methyltransferases.

The present invention is also directed to a method for reprogramming a eukaryotic cell. The method comprises, as step (a), specifically suppressing expression, activity, or expression and activity of DNA methyltransferases within a eukaryotic cell; and simultaneously, as step (b), increasing expression, activity, or both expression and activity of glycine-N-methyl transferase within the eukaryotic cell. Step (a) can comprise contacting the cell with a suppression-effective amount of a siRNA dimensioned and configured to suppress expression of DNA methyltransferases. Step (a) can also comprise contacting the cell with a suppression-effective amount of a siRNA dimensioned and configured to suppress to reduce 5-methylated cytosines in DNA in the cell by at least about 5%. Step (b) can comprise contacting the cell with an amount of a retinoic acid effective to increase expression, activity, or both expression and activity of glycine-N-methyl transferase within the cell. Step (b) can also comprise contacting the cell with all-trans retinoic acid. Further, step (b) can include contacting the cell with a compound that binds a retinoic acid receptor. In addition to steps (a) and (b), the method can includes, as step (c), specifically suppressing within the cell expression, activity, or expression and activity of an enzyme selected from the group consisting of 5,10-methylenetetrahydrofolate reductase and cystathione-beta-synthase. It is within the scope of the present invention to contact the cell with a siRNA selected from the group consisting of SEQ. ID. NOS: 1-41.

The present invention is further directed to a method to change differentiation potential in a eukaryotic cell. Here, the method comprises contacting the eukaryotic cell in vitro with an amount of a siRNA, wherein the siRNA is dimensioned and configured to suppress expression of DNA methyltransferases specifically, provided that the siRNA does not suppress expression of glycine-N-methyl transferase, and wherein the amount is effective to induce genome-wide DNA demethylation, wherein cellular differentiation potential is increased. The eukaryotic cells are selected from the group consisting of stem cells, progenitor cells, somatic cells, and cells subjected to somatic cell nuclear transfer (NT cells). This methods comprises contacting the cell with a siRNA that is dimensioned and configured to suppress specifically the expression of a DNA methyltransferase selected from the group consisting of DNA methyltransferase 1 (Dnmt 1), DNA methyltransferase 3a (Dnmt 3a), and DNA methyltransferase 3b (Dnmt 3b). The method further comprises contacting the cell with an amount of a compound effective to increase expression of, activity of, or both expression of and activity of, glycine-N-methyl transferase, such as retinoic acid or all-trans retinoic acid. The cells can also be contacted with a composition comprising, in combination, the siRNA and all-trans retinoic acid.

The present invention is further directed to a method to increase differentiation potential in a differentiated cell, the method comprising contacting a differentiated cell, in vitro, with a composition comprising, in combination, as step (i) a knockdown-effective amount of a small-interfering ribonucleic acid (siRNA), wherein the siRNA is dimensioned and configured to suppress expression of DNA methyltransferases specifically; (ii) a knockdown-effective amount of a siRNA dimensioned and configured to suppress expression of an enzyme selected from the group consisting of 5,10-methylenetetrahydrofolate reductase and cystathione-beta-synthase; and (iii) a compound effective to increase expression of, activity of, or both expression of and activity of, glycine-N-methyl transferase, wherein the cell is contacted with the composition for a time effective to induce genome-wide DNA demethylation within the cell, whereby cellular differentiation potential is increased. The method comprises contacting the cell with a composition comprising a siRNA that is dimensioned and configured to suppress specifically the expression of a DNA methyltransferase selected from the group consisting of DNA methyltransferase 1 (Dnmt 1), DNA methyltransferase 3a (Dnmt 3a), and DNA methyltransferase 3b (Dnmt 3b). The compound effective to increase expression of, activity of, or both expression of and activity of glycine-N-methyl transferase, is retinoic acid or all-trans retinoic acid. The cells are contacted with a siRNA selected from the group consisting of SEQ. ID. NOS: 1-41.

The present invention is further directed to a method for determining the developmental potential of a cell. The method comprises determining SAM-to-SAH ratio in the cell, wherein a SAM-to-SAH ratio of less than about 1.0 indicates increased developmental potential of the cell. The method comprises measuring methylation of cytosine residues present in the DNA of the cell, wherein methylation less than about 10% indicates increased developmental potential of the cell.

The present invention further comprises a method for controlling differentiation potential in a cell, the method comprising, as step (a) maintaining SAM-to-SAH ratio in the cell to less than about 1.0; and (b) maintaining methylation of cytosine residues in DNA of the cell to less than about 40%. The method further comprises, as step (a) maintaining the SAM-to-SAH ratio in the cell to less than about 0.5; and, as step (b) maintaining the methylation of cytosine residues in DNA of the cell to less than about 20%.

The present invention is further directed to a cell culture medium for increasing differentiation potential in a differentiated cell disposed within the culture medium. The culture medium comprises a base medium sufficient to maintain viability of the cell, in combination with a factor that reduces activity of methyl donors present in the cell culture medium. The factor is selected from the group consisting of homocysteine and all-trans retinoic acid. Alternatively, the factor is a suppression-effective amount of a siRNA dimensioned and configured to suppress expression of DNA methyltransferases.

The present invention is also directed to a method for identifying compounds that affect cell differentiation. The method comprises, as step (a), reducing percentage of cytosines in DNA of a cell that are methylated by at least about 5%, wherein the cell has a first phenotype prior to the reduction; and, as step (b), reducing SAM-to-SAH ratio in the cell to less than about 1.0; and, as step (c) contacting the cell with a compound suspected of affecting cell differentiation; and, as step (d) comparing the first phenotype of the cell to phenotype of the cell after step (c), wherein appearance after step (c) of a phenotype different from the first phenotype indicates that the compound has an affect on cell differentiation. Step (a) can include reducing the percentage of cytosines in the DNA of the cell that are methylated by at least about 5%. Step (a) can also include reducing the percentage of cytosines in the DNA of the cell that are methylated by at least about 10%. The cell can include a reporter system to monitor changes in transcription, which measures presence of an enzyme activity selected from the group consisting of luciferase activity, beta-lactamase activity, and beta-galactosidase activity The present invention is further directed to a method of restoring cell differentiation potential comprising:

(a) reducing DNA methylation in somatic cell nuclei, cells, and/or specific parts of cells by reducing methyl donors in vitro;

(b) increasing expression of GNMT gene and/or enzyme activity that result in decreased SAM:SAH ratio and decreased levels of DNA methylation;

(c) reducing SAM:SAH ratio by reducing expression and/or activity of specific enzymes such as MTHFR and/or cystathione-beta-synthase (Cbs);

(d) reducing the activity of DNA methyltransferases including Dnmts 1, 3a and/or 3b;

(e) increasing homocysteine and/or SAH levels in vitro, glucagons, or related factors to lower the SAM:SAH ratio (reduced SAM: SAH will lower methylation);

(f) depleting glutathione levels to decrease SAM:SAH ratio;

(g) developing defined media that incorporate one or more of the above factors to reduce methylation (medias deficient in methyl donors, medias with additional homocysteine, etc.);

(h) developing a new assay based on using a beta-lactamase reporter gene and/or other viable reporter genes (luciferase, beta glucosidase, or others) to identify factors that induce transcription of the GNMT gene, or that identify other factors or activities that stimulate GNMT activity; and (i) developing a new assay based on using a beta-lactamase reporter gene and/or other viable reporter genes (luciferase, beta glucosidase, or others) to identify factors that reduce transcription of the DNA methyltransferase genes, or that identify other factors or activities that reduce the activity of DNA methyltransferases.

The invention includes but is not limited to:

(a) new research tools including specialized media and cell culture that enable in vitro production of reprogrammed cells with restored differentiation potential (totipotential, pluripotential, multipotential) by demethylating the genome;

(b) new stem-like cells produced by these media and cultures, that can be used for research or therapeutic applications;

(c) a new assay system for monitoring GNMT expression using a beta lactamase reporter gene, luciferase, beta galactosidase, and/or other relevant reporter genes, to assess the impact of GNMT expression or other activity on restoring differentiation potential of the cell;

(d) a new assay system for monitoring DNA methyltransferase expression using a beta lactamase reporter gene, luciferase, beta galactosidase, and/or other relevant reporter genes, to assess the impact of DNA methyltransferase expression or other activity on restoring differentiation potential of the cell;

(e) improving the efficiency of somatic cell nuclear transfer; and (f) improving the derivation of embryonic stem cells from SCNT reconstructed embryos (or units).

The embodiments include:

(a) treating existing commercial or other media with ATRA, which increases GNMT transcription and activity, lowers the SAM:SAH ratio and decreases methylation potential of cells and restores differentiation and/or developmental potential;

(b) modifying existing commercial or other media to enable knock down of DNA methyltransferases 1, 3a, and/or 3b using interfering RNA technology resulting in reduced levels of DNA methylation;

(c) modifying existing commercial or other media to enable knock down of MTHFR and/or Cbs using interfering RNA technology, antisense, or other knock down technologies resulting in decreased SAM:SAH ratio and DNA methylation;

(d) modifying existing commercial or other media to increase the transcription, protein expression and activity of GNMT resulting in decreased SAM:SAH ratio and DNA methylation;

(e) modifying existing commercial or other media to decrease SAM:SAH ratio by altering levels of methyl donors and/or homocysteine and/or SAH.

Without wishing to be held to one explanation for the rationale behind the present invention, it is believed that methyl groups provided from the diet, culture media, or the folate-dependent one-carbon pool are essential for normal function. Methyl group deficiency leads to down-regulation of transmethylation reactions. Methyl groups supplied from the diet (or culture media), in the form of choline and methionine or from the folate-dependent one-carbon pool, must be activated to SAM to serve as substrates in numerous transmethylation reactions. Because SAH is a product of transmethylation reactions and a potent inhibitor of most SAM-dependent methyltransferases, the ratio of SAM/SAH is an important index of transmethylation potential. Therefore, the intracellular supply of SAM is critical for transmethylation, but the regulation of this ratio is important as well.

The cytosolic enzyme GNMT functions to optimize transmethylation reactions by regulating the SAM/SAH ratio. When methyl groups are abundant and SAM levels elevated, GNMT disposes of the excess methyl groups by forming the essentially inactive metabolite sarcosine from glycine. SAM also reduces the supply of methyl groups originating from the one-carbon pool by inhibiting MTHFR, the enzyme responsible for the synthesis of 5-methyl-THF, the folate coenzyme that donates its methyl group to homocysteine to form methionine. Because 5-methyl-THF also binds to GNMT and inhibits its activity, a decrease in 5-methyl-THF levels due to inhibition of MTHFR by SAM results in an increase in the activity of GNMT. Conversely, under conditions of decreased methyl groups and SAM, the inhibition of MTHFR is removed, leading to an increase in 5-methyl-THF concentrations and subsequent inhibition of GNMT. This ensures that methyl groups are conserved for important transmethylation reactions when methyl group availability is compromised. Therefore, factors that inappropriately activate GNMT may lead to the down regulation of numerous methyltransferases that are important in the maintenance of an appropriate methylation state.

The present invention was driven by the need to accelerate development of new, more effective, efficient methods of cell reprogramming. Such methods impact the discovery and development of therapeutically valuable cells, including stem cells, new research tools for accelerating stem cell and other cell-based therapy research, propagation of valuable or endangered animals, and production of high value genetically engineered animals.

The invention is directed towards resolving problems with current methods for dedifferentiating cells, and redifferentiating them into new cells. Specifically, current methods, primarily based on SCNT, are highly inefficient, and produce unreliable results. The new invention avoids the use of nuclear transfer, and its associated limitations. SCNT units exhibit defects in regulating DNA methylation, including deficiencies in global demethylation, which contributes to inefficient cell reprogramming. The present invention overcomes this specific problem.

The present invention also will enable and improve the efficiency of SCNT for the production of endangered animals, value added livestock and derivation of ES cells by improving the dedifferentiation (global demethylation) process required after reconstruction.

The invention also will enable development of new cell-based therapeutics that overcomes the critical problems of immune rejection and limited source of material associated with the use of embryonic stem cells. By enabling the use of a patient's own somatic cells for dedifferentiation and redifferentiation into new cell types, the invention will provide an immuno-compatible source of cells, from a wide variety of starting cell types.

Moreover, the field of stem cell research is highly limited at the current time by inadequate cell cultures and media for maintaining cells in dedifferentiated states, or for directing cells to differentiate along specific lineages. The pathways, proteins, and related molecules associated with the new invention will enable development of new cultures and media that overcome these limitations. Similarly, the present invention will provide new markers of differentiation and redifferentiation, and the ability to produce new differentiated cell lines that will speed drug discovery by providing and enhancing new approaches for screening regenerative medicine drug candidates.

The field of cell-based therapeutics is highly limited at the current time due to limited sources of starting material and expensive methods of isolation and expansion under GMP/GML guidelines. For example, in the case of new cell therapy applications involving transplantation of islet cells to produce insulin in diabetic patients, current methods required at least two cadaver donors provide sufficient cells for just one patient. The present invention is directed at overcoming these shortcomings by significantly improving the amount of starting material and desired product to be used. Moreover, such cells carry an inherent risk of inducing adverse immune rejection in the recipient. The present invention is directed at overcoming this problem by offering the opportunity to use a patient's own cells as the source of starting material.

The present invention is directed towards methods that can accelerate the progress of reprogramming by regulating DNA methylation. Methods aimed at altering the expression and/or activity of DNA methyltransferases could have significant effects increasing the efficiency of reprogramming by altering the SAM:SAH ratio. One approach is to alter the regulation of methyl group metabolism by specifically altering the expression of key enzymes using compounds such as retinoic acid (RA) and retinoids. Administration of ATRA and other retinoid compounds induces and activates GNMT, compromising SAM-dependent transmethylation reactions, including the methylation of DNA, resulting in hypomethylation of genomic DNA. Others have used methylation inhibitors, such as 5-azacytidine and 5-aza-2'-deoxycytidine to decrease DNA methylation levels and provide antitumor effects [82].

Another method is to overexpress a demethylase in somatic cells in culture. To date, an active demethylase has not been validated.

The key advantages of the present invention over prior methods include:

The invention does not involve the use of nuclear transfer, thus avoids the high level of inefficiency in nuclear reprogramming and actual cell development.

The invention does not rely upon the use of embryonic stem cells as starting materials for cell differentiation. Thus, it overcomes a critical limiting barrier in availability of starting material.

The invention can be used to improve embryonic and adult stem cell culture systems to minimize spontaneous differentiation.

The invention does not rely upon embryonic stem cells or other foreign materials for development of new regenerative cell therapies, and thus minimizes the potential for immune rejection by the patient.

The invention exploits natural metabolic processes by a simple nutritional approach, thus reducing the number of complicating factors that could contribute to failure, such as the cytotoxic affects induced by compounds such as 5'-azacytidine and azacitadine (also known as Aza C and manufactured under the trademark VIDAZA by Pharmion of Boulder, Colo.) or requiring a genetic alteration such as overexpressing an active demethylase using a transgene system.

The invention can be used to improve SCNT.

The invention can be used to more efficiently improve the derivation of ES cells from SCNT-generated embryos (units).

The objects and advantages of the invention will appear more fully from the following detailed description of the preferred embodiment of the invention made in conjunction with the accompanying drawings.

BRIEF DESCRIPTION OF THE DRAWINGS

FIG. 3A shows cells after treatment with ATRA. FIG. 3B shows cells after positive staining with oil red-0 (a common stain for lipids) following ATRA treatment. See Example 2.

FIG. 4A depicts cells that tested positive for osteoblast-like cells with alkaline phosphatase staining. FIG. 4B depicts cells exhibiting calcium phosphate mineralization with alizarin staining.

FIG. 6A depicts the specific knock down of Dnmt1 using a Dnmt1 siRNA. FIG. 6B depicts the specific knock down of lamin using a lamin siRNA.

FIG. 7A depicts real time PCR results showing a 79% decrease in Dnmt3b mRNA levels as compared to controls. FIG. 7B depicts HPLC results showing a 52% relative reduction in methylated cytosine in the cells.

ABBREVIATIONS AND DEFINITIONS

Figure 1:
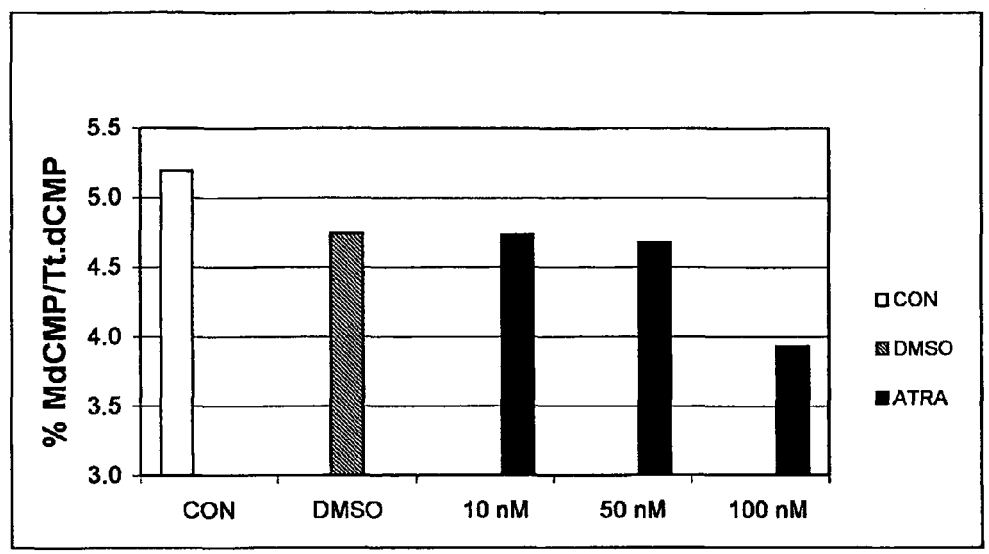
FIG. 1 is a graph depicting relative levels of cytosine methylation in bovine serial nuclear transfer donor somatic cells after growth to confluence in growth media alone (CON), growth media treated with DMSO (DMSO), and growth media treated with all-trans retinoic acid (ATRA). See Example 1.

Unless otherwise described herein, the following definitions and abbreviations will apply throughout this disclosure:

ATRA means all-trans retinoic acid.

Cbs means cystathione-beta-synthase.

Cell Reprogramming means the process by which a terminally differentiated cell can be restored to a state where it has the potential to differentiate into a new cell type.

Culture Medium or Growth Medium means a suitable medium capable of supporting growth of cells.

Demethylating Culture Medium or Demethylating Growth Medium means a suitable medium capable of supporting growth of cells in a manner that induces demethylation of DNA.

Differentiation means the process by which cells become structurally and functionally specialized during embryonic development.

DMSO means dimethyl sulfoxide.

DNA means deoxyribonucleic acid.

DNA Methylation means the attachment of a methyl group (a —CH3 group) to a cytosine (one of four nitrogenous bases found in DNA) in a eukaryotic DNA. This is done routinely, as a way to protect self DNA from the enzymes and chemicals produced to destroy foreign DNA, and as a way to regulate transcription of genes in the DNA.

DNMT means DNA methyltransferase.

Epigenetics refers to the state of DNA with respect to heritable changes in function without a change in the nucleotide sequence. Epigenetic changes can be caused by modification of the DNA, such as by methylation and demethylation, without any change in the nucleotide sequence of the DNA.

FRET means fluorescence resonance energy transfer.

GAPDH means glyceraldehyde-3-phosphate dehydrogenase.

GNMT means glycine-N-Methyltransferase.

H3K4me means methylation of histone H3 at Lys4.

H3K9me2/3 means di/trimethylation of specific lysine residues such as lysine 9 on histone H3.

Histone means a class of protein molecules found in chromosomes responsible for compacting DNA enough so that it will fit within a nucleus. Prokaryotes do not have histones. However, the DNA of the genus *Thermoplasma* (a cell-wallless member of the domain Archaea) is surrounded by a highly basic DNA-binding protein which strongly resembles the eukaryotic histones.

IBMX means isobutylmethylxanthine.

ICM means inner cell mass.

"Knock down" means to suppress the expression of a gene in a gene-specific fashion. A cell that has one or more genes "knocked down," is referred to as a knock-down organism or simply a "knock-down."

MDS means myelodysplastic syndrome.

MTHFR means 5,10-methylenetetrahydrofolate reductase.

Oocyte means a developing female reproductive cell which divides by meiosis into four haploid cells, forming one ovum that can be fertilized by a sperm cell.

Pluripotent means capable of differentiating into cell types of the 3 germ layers or primary tissue types.

RA means retinoic acid.

Reprogramming means removing epigenetic marks in the nucleus, followed by establishment of a different set of epigenetic marks. During development of multicellular organisms, different cells and tissues acquire different programs of gene expression.

These distinct gene expression patterns appear to be substantially regulated by epigenetic modifications such as DNA methylation, histone modifications and other chromatin binding proteins [22, 23]. Thus each cell type within a multicellular organism has a unique epigenetic signature which is conventionally thought to become "fixed" and immutable once the cells differentiate or exit the cell cycle. However, some cells undergo major epigenetic "reprogramming" during normal development or certain disease situations.

RNA means ribonucleic acid.

RT-PCR means reverse transcribed polymerase chain reaction.

SAH means S-adenosylhomocysteine.

SAM means S-adenosylmethionine.

SCNT means somatic cell nuclear transfer.

siRNA means small interfering RNA, also known as short interfering RNA or silencing RNA.

Somatic cells mean any of the cells of an organism that have differentiated into the tissues, organs, etc. of the body (as opposed to germ cell—any of various cells, especially an egg or sperm cell, from which a new organism can develop).

TE means trophoectoderm.

Totipotent means capable of developing into a complete embryo or organ.

TZD means Thiazolidinedione.

DETAILED DESCRIPTION OF THE INVENTION

The present invention involves inducing demethylation of a patient's adult stem cells or fully differentiated somatic cells in a manner that restores differentiation potential and can be used as an autologous source of therapeutic cells; or, using the demethylated cells to improve the efficiency of SCNT and to more efficiently generate patient-specific ES cells to be used for therapeutic purposes.

The present invention is specifically directed to specialized cell lines and a specialized cell culture. The methods for achieving both are critical to the invention. In its basic sense, the methods involve demethylation steps that yield reprogrammed cell lines. The factors that enable demethylation are included in the cell culture medium, which is used to produce cells that can be differentiated into new cell types.

The present invention is directed to cell culture medium to which ATRA and/or siRNA can be added, or components adjusted sufficiently, to reduce DNA methylation levels to such an extent as to restore differentiation and/or developmental potential either by inducing with specific differentiation factors such as, but not limited to cytokines, growth factors, transcription factors and/or using the demethylated cells for SCNT.

The invention is directed to in vitro production of reprogrammed cells which have had differentiation potential (totipotential, pluripotential, multipotential) restored by demethylating the genome. The embodiments include:

(a) treating with ATRA, siRNA, and/or similar or related molecules;
(b) knocking down DNA methyltransferases 1, 3a, and/or 3b using interfering RNA technology, antisense, or other mechanisms for inhibition;
(c) knocking down MTHFR and/or Cbs using interfering RNA technology;
(d) increasing the transcription, protein expression and activity of GNMT;
(e) increasing levels of homocysteine in vitro;
(f) increasing levels of SAH;
(g) decreasing levels of SAM;
(h) decreasing levels of methyl donors such as, but not limited to, folate, methionine, choline, betaine, vitamins B6 and B12;
(i) using the cells to improve SCNT; and
(j) using the cells to more efficiently derive ES cells from SCNT reconstructed units (embryos).

Cells: For purposes of the present invention, the term "cell" or "cells," unless specifically limited to the contrary, includes any somatic cell, embryonic stem (ES) cell, adult stem cell, nuclear transfer (NT) units, and stem-like cells. A promising source of organs and tissues for transplantation lies in the development of stem cell technology. Theoretically, stem cells can undergo self-renewing cell division to give rise to phenotypically and genotypically identical daughters for an indefinite time and ultimately can differentiate into at least one final cell type. By generating tissues or organs from a patient's own cells, transplant tissues can be generated to provide the advantages associated with xenotransplantation without the associated risk of infection or tissue rejection.

Stem cells also provide promise for improving the results of gene therapy. A patient's own stem cells could be genetically altered in vitro, then reintroduced in vivo to produce a desired gene product. These genetically altered stem cells would have the potential to be induced to differentiate to form a multitude of cell types for implantation at specific sites in the body, or for systemic application. Alternately, heterologous stem cells could be genetically altered to express the recipient's major histocompatibility complex (MHC) antigen, or no MHC, to allow transplant of those cells from donor to recipient without the associated risk of rejection.

Stem cells are defined as cells that have extensive and indefinite proliferation potential that differentiate into several cell lineages, and that can repopulate tissues upon transplantation. The quintessential stem cell is the embryonal stem (ES) cell, as it has unlimited self-renewal and pluripotent differentiation potential. These cells are derived from the inner cell mass of the blastocyst, or can be derived from the primordial germ cells from a post-implantation embryo (embryonal germ cells or EG cells). ES and EG cells have been derived from mouse, and more recently also from non-human primates and humans. When introduced into mouse blastocysts or blastocysts of other animals, ES cells can contribute to all tissues of the mouse (animal). When transplanted in post-natal animals, ES and EG cells generate teratoma, which again demonstrates their pluripotency. ES and EG cells can be identified by positive staining with the antibodies SSEA1 and SSEA4.

At the molecular level, ES and EG cells express a number of transcription factors highly specific for these undifferentiated cells. These include Oct-4 and Rex-1. Also found are the LIF-R and the transcription factors Sox-2 and Rox-1, even though the latter two are also expressed in non-ES cells. Oct-4 is a transcription factor expressed in the pregastrulation embryo, early cleavage stage embryo, cells of the inner cell mass of the blastocyst, and in embryonic carcinoma (EC) cells. Oct-4 is down-regulated when cells are induced to differentiate in vitro and in the adult animal oct-4 is only found in germ cells. Several studies have shown that Oct-4 is required for maintaining the undifferentiated phenotype of ES cells, and plays a major role in determining early steps in embryogenesis and differentiation. Oct-4, in combination with Rox-1, causes transcriptional activation of the Zn-finger protein Rex-1, and is also required for maintaining ES in an undifferentiated state. Likewise, Sox-2 is needed together with Oct-4 to retain the undifferentiated state of ES/EC cells and to maintain murine (but not human) ES cells. Human or murine primordial germ cells require presence of LIF. Another hallmark of ES cells is presence of telomerase, which provides these cells with an unlimited self-renewal potential in vitro.

Stem cells have been identified in several organ tissues. The best characterized is the hematopoietic stem cell. This is a mesoderm-derived cell that has been purified based on cell surface markers and functional characteristics. The hematopoietic stem cell, isolated from bone marrow, blood, cord blood, fetal liver and yolk sac, is the progenitor cell that reinitiates hematopoiesis for the life of a recipient and generates multiple hematopoietic lineages [93-100]. When transplanted into lethally irradiated animals or humans, hematopoietic stem cells can repopulate the erythroid, neutrophil-macrophage, megakaryocyte and lymphoid hemopoietic cell pool. In vitro, hemopoietic stem cells can be induced to undergo at least some self-renewing cell divisions and can be induced to differentiate into the same lineages as is seen in vivo. Therefore, this cell fulfills the criteria of a stem cell. Stem cells which differentiate only to form cells of hematopoietic lineage, however, are unable to provide a source of cells for repair of other damaged tissues, for example, heart or lung tissue damaged by high-dose chemotherapeutic agents.

A second stem cell that has been studied extensively is the neural stem cell [101-103]. Neural stem cells were initially identified in the subventricular zone and the olfactory bulb of fetal brain. Until recently, it was believed that the adult brain no longer contained cells with stem cell potential. However, several studies in rodents, and more recently also non-human primates and humans, have shown that stem cells continue to be present in adult brain. These stem cells can proliferate in vivo and continuously regenerate at least some neuronal cells in vivo. When cultured ex vivo, neural stem cells can be induced to proliferate, as well as to differentiate into different types of neurons and glial cells. When transplanted into the brain, neural stem cells can engraft and generate neural cells and glial cells. Therefore, this cell too fulfills the definition of a stem cell.

A third tissue specific cell that has been named a stem cell is the mesenchymal stem cell (MSC), initially described by Fridenshtein [104]. Mesenchymal stem cells, originally derived from the embryonal mesoderm and isolated from adult bone marrow, can differentiate to form muscle, bone, cartilage, fat, marrow stroma, and tendon. During embryogenesis, the mesoderm develops into limb-bud mesoderm, tissue that generates bone, cartilage, fat, skeletal muscle and possibly endothelium. Mesoderm also differentiates to visceral mesoderm, which can give rise to cardiac muscle, smooth muscle, or blood islands consisting of endothelium and hematopoietic progenitor cells. Primitive mesodermal or mesenchymal stem cells, therefore, could provide a source for a number of cell and tissue types. A number of mesenchymal stem cells have been isolated [105-117]. Of the many mesenchymal stem cells that have been described, all have demonstrated limited differentiation to form only those differentiated cells generally considered to be of mesenchymal origin.

To date, the most multipotent mesenchymal stem cell reported is the cell isolated by Pittenger, et al [118], which expresses the $SH2^+SH4^+CD29^+CD44^+CD71^+CD90^+CD106^+CD120a^+CD124^+CD14^-CD34^-CD45^-$ phenotype. This cell is capable of differentiating to form a number of cell types of mesenchymal origin, but is apparently limited in differentiation potential to cells of the mesenchymal lineage, as the team who isolated it noted that hematopoietic cells were never identified in the expanded cultures.

Other stem cells have been identified, including gastrointestinal stem cells, epidermal stem cells, and hepatic stem cells, also termed oval cells [119-121]. Most of these are less well characterized.

Compared with ES cells, tissue specific stem cells have less self-renewal ability and, although they differentiate into multiple lineages, they are not pluripotent. No studies have addressed whether tissue specific cells express markers described above of ES cells. In addition, the degree of telomerase activity in tissue specific stem cells has not been fully explored, in part because large numbers of highly enriched populations of these cells are difficult to obtain.

Until recently, it was thought that organ specific stem cells could only differentiate into cells of the same tissue. A number of recent publications have suggested that adult organ specific stem cells may be capable of differentiating into cells of different tissues. A number of studies have shown that cells transplanted at the time of a bone marrow transplant can differentiate into skeletal muscle [122-123]. This could be considered within the realm of possible differentiation potential of mesenchymal cells that are present in marrow. Jackson published that muscle satellite cells can differentiate into hemopoietic cells, again a switch in phenotype within the splanchnic mesoderm [124]. Other studies have shown that stem cells from one embryonal layer (for instance splanchnic mesoderm) can differentiate into tissues thought to be derived during embryogenesis from a different embryonal layer. For instance, endothelial cells or their precursors detected in humans or animals that underwent marrow transplantation are at least in part derived from the marrow donor [125-126]. Thus, visceral mesoderm and not splanchnic mesoderm, such as MSC, derived progeny are transferred with the infused marrow. Even more surprising are the reports demonstrating both in rodents and humans that hepatic epithelial cells and biliary duct epithelial cells are derived from the donor marrow [127-129]. Likewise, three groups have shown that neural stem cells can differentiate into hemopoietic cells. Finally, Clarke et al. reported that neural stem cells injected into blastocysts can contribute to all tissues of the chimeric mouse [130].

Transplantation of tissues and organs generated from heterologous embryonic stem cells requires either that the cells be further genetically modified to inhibit expression of certain cell surface markers, or that the use of chemotherapeutic immune suppressors continue in order to protect against transplant rejection. Thus, although embryonic stem cell research provides a promising alternative solution to the problem of a limited supply of organs for transplantation, the problems and risks associated with the need for immunosuppression to sustain transplantation of heterologous cells or tissue would remain. An estimated 20 immunologically different lines of embryonic stem cells would need to be established in order to provide immunocompatible cells for therapies directed to the majority of the population [132].

Using cells from the developed individual, rather than an embryo, as a source of autologous or allogeneic stem cells would overcome the problem of tissue incompatibility associated with the use of transplanted embryonic stem cells, as well as solve the ethical dilemma associated with embryonic stem cell research. The greatest disadvantage associated with the use of autologous stem cells for tissue transplant thus far lies in their limited differentiation potential. A number of stem cells have been isolated from fully-developed organisms, particularly humans, but these cells, although reported to be multipotent, have demonstrated limited potential to differentiate into multiple cell types.

Even though stem cells with multiple differentiation potential have been isolated previously by others, a demethylated cell with the potential to differentiate into a wide variety of cell types of different lineages, including fibroblasts, osteoblasts, chondrocytes, adipocytes, skeletal muscle, endothelium, stroma, smooth muscle, cardiac muscle, nueral cells and hemopoietic cells, has not been described. If cell and tissue transplant and gene therapy are to provide the therapeutic advances expected, a demethylated cell with restored or expanded differentiation and/or developmental potential is needed, either as a source for patient specific therapeutic cells, or as a more efficient donor cell for SCNT, or as an object for screening of differentiation factors or compounds that might be used to assist in inducing differentiation along specific lineages.

Cell Culture Media: The present invention utilizes cell culture media, growth factors, and methods for inducing DNA demethylation of cells and growing and maintaining cultures of demethylated cells. The media provides for the growth and maintenance of cells and can be used to screen for additional factors and useful combinations of factors. The ability to grow cells in a substantially undifferentiated state using the cell culture media, growth factors, and methods provided herein provides important benefits including the ability to produce cell lines having multiple genetic modifications (as in the application of gene therapy) with important therapeutic applications.

The cell culture media may include a growth medium that is effective to support the growth of demethylated cells; a nutrient serum effective to support the growth of demethylated cells; non-essential and essential amino acids, and a pyruvate salt. Optionally, the cell culture media may also include a reducing agent.

Another non-limiting example of a suitable culture medium useful in practicing the present invention includes a variety of growth media prepared with a base of Dulbecco's minimal essential media (DMEM). The DMEM can be supplemented with a variety of supplements including fetal calf serum, glutamine and/or sodium pyruvate. Preferably the DMEM includes 15% fetal calf serum, 2 mM glutamine and 1 mM sodium pyruvate.

Another example of a suitable culture medium is glucose- and phosphate-free modified human tubal fluid media (HTF) supplemented with 15% fetal calf serum, 0.2 mM glutamine, 0.5 mM taurine, and 0.01 mM each of the following amino acids: asparagine, glycine, glutamic acid, cysteine, lysine, proline, serine, histidine, and aspartic acid.

Growth Factor: The growth medium can include any serum or serum-based solution that supplies nutrients effective to maintain the growth and viability of demethylated cells. Examples of such serum include, without limitation, fetal bovine serum (FBS) and fetal calf serum (FCS). For example, the FBS may be provided in a concentration of between about 1% and about 25%. In particular, the FBS may be provided in a concentration of between about 2.5% and about 20%. In one embodiment, demethylated cells are grown in 10% FBS.

A growth factor may also be provided to assist in the derivation and maintenance of cultures of demethylated cells in a substantially undifferentiated state. The identities and effective concentrations of such growth factors can be determined using the methods as described herein or using techniques known to those of skill in the art of culturing cells. For example, one or more of the following factors can be used at the stated final concentration: forskolin ([3R-(3α,4αβ,5B,6B,6a α,10α,10αβ,10α)]-5-(acetyloxy)-3-ethenyldodecahydro-6,10,10b-trihydroxy-3,4-a,7,7,10a-pentamethyl-1H-naphtho[2,1-b]pyran-1-one) at 10 μM, cholera toxin at 10 μM, isobutylmethylxanthine (IBMX) at 0.1 mM, dibutyrladenosine cyclic monophosphate (dbcAMP) at 1 mM. In another embodiment, the growth factor is basic fibroblast growth factor (bFGF), more specifically, human recombinant basic fibroblast growth factor (bFGF), in the range of about 1-10 ng/ml.

Another factor is growth media harvested from cultures of human embryonal carcinoma (EC) cells. In a particular example, human NTERA-2 EC cells (ATCC accession number CRL 1973) are grown to confluence in DMEM supplemented with 10% fetal calf serum or mouse ES cells are grown to confluence in DMEM supplemented with 15% fetal calf serum, 2 mM glutamine, 1000 U/ml LIF. Growth media is harvested daily over several days, passed through a 0.22 micron filter and frozen at −80° C. This human EC or mouse ES "conditioned" media is added to the demethylated growth media in empirically determined amounts, as judged by the effect on demethylated cell growth and viability.

In another embodiment the growth media includes ligands for receptors that activate the signal transduction gp130, either by binding to a receptor that associates with gp 130 or by binding directly to and activating gp 130. For example, human recombinant leukemia inhibitory factor (LIF) at about 1000 U/ml to 2000 U/ml or oncostatin-M at 10 U/ml, can be used.

Tissue Culture Antibiotics: Typically, embryonal germ (EG) medium also contains commonly used tissue culture antibiotics, such as penicillin and streptomycin. An effective amount of factors are then added daily to either of these base solutions to prepare human EG growth media of the instant invention. The term "effective amount" means the amount of such described factor as to permit a beneficial effect on human EG growth and viability of human EG cells using judgment common to those of skill in the art of cell culturing and by the teachings supplied herein.

Typically, the demethylating culture medium also contains commonly used tissue culture antibiotics, such as penicillin and streptomycin. An effective amount of these factors are then added daily to either of these base solutions to prepare demethylating growth media of the instant invention. The term "effective amount" as used herein is the amount of such described factor as to permit a beneficial effect on demethylation and viability of cells using judgment common to those of skill in the art of cell culturing and by the teachings supplied herein.

Ranges: Table 1 provides ranges for the ingredients useful in the cell culture medium of the present invention.

TABLE 1

| | Medium | | |
|---|---|---|---|
| | Most preferable | Preferable | Acceptable |
| | | Working pH range | |
| Component | 7.0-7.4 mg/L | 7.0-7.4 mg/L | 7.0-7.4 mg/L |
| CaCl (anhyd.) | 200.00 | 50-350 | 1-500 |
| Fe(NO$_3$)3—9H$_2$O | 0.10 | 0.01-0.2 | 0.001-1.0 |
| KCl | 400.00 | 100-600 | 1-1000 |

TABLE 1-continued

| | Medium | | |
|---|---|---|---|
| | Most preferable | Preferable | Acceptable |
| | | Working pH range | |
| Component | 7.0-7.4 mg/L | 7.0-7.4 mg/L | 7.0-7.4 mg/L |
| MgSO$_4$ (anhyd.) | 97.67 | 10-250 | 1-500 |
| NaCl | 6400.00 | 5000-8000 | 1000-10000 |
| NaHCO$_3$ | 3700.00 | 2000-6000 | 500-10000 |
| NaH$_2$PO$_4$—H$_2$O | 125.00 | 50-250 | 1-500 |
| D-Glucose | 1000.00 | 1000-5000 | 1-10000 |
| Phenol Red | 15.00 | 15.00 | 15.00 |
| Sodium Pyruvate | 110.00 | 10-200— | 1-1000 |
| L-Arginine-HCl | 84.00 | 50-150 | 10-500 |
| L-Glutamine | 584.00 | 300-600 | 100-900 |
| Glycine | 30.00 | 10-60 | 1-100 |
| L-Histadine-HCl—H$_2$O | 42.00 | 10-100 | 1-1000 |
| L-Isoleucine | 105.00 | 10-250 | 1-500 |
| L-Leucine | 105.00 | 10-250 | 1-500 |
| L-Lysine-HCl | 146.00 | 10-250 | 1-500 |
| L-Methionine | 30.00 | 10-100 | 1-500 |
| L-Phenylalanine | 66.00 | 10-100 | 1-500 |
| L-Serine | 42.00 | 10-100 | 1-500 |
| L-Threonine | 95.00 | 50-250 | 1-500 |
| L-Tryptophan | 16.00 | 5-50 | 1-100 |
| L-Tyrosine-2Na—2H$_2$O | 104.00 | 10-500 | 1-900 |
| L-Valine | 94.00 | 50-150 | 10-500 |
| D-Ca pantothenate | 4.00 | 1-10 | 0.1-50 |
| Chlorine Chloride | 4.00 | 1-10 | 0.1-50 |
| Folic Acid | 4.00 | 1-10 | 0.1-50 |
| i-Inositol | 7.20 | 1-10 | 0.1-50 |
| Niacinamide | 4.00 | 1-10 | 0.1-50 |
| Pyridoxal-HCl | 4.00 | 1-10 | 0.1-50 |
| Riboflavin | 0.40 | 1-10 | 0.1-50 |
| Thiamine-HCl | 4.00 | 1-10 | 0.1-50 |

An example of a cell culture medium which can be used in the present invention is alpha-MEM (Chemicon International, Temecula Calif.) as described in the following Table 2:

TABLE 2

| Component | Working pH range 7.0-7.4 mg/L |
|---|---|
| Inorganic Salts | |
| CaCl$_2$ (anhyd.) | — |
| KCl | 400.00 |
| KH$_2$PO$_4$ | — |
| MgCl$_2$ (anhyd.) | 94.70 |
| MgSO$_4$ (anhyd.) | — |
| NaCl | 6500.00 |
| NaHCO$_3$ | 2000.00 |
| NaH$_2$PO$_4$—H$_2$O | 1154.00 |
| NaH$_2$PO$_4$ (anhyd.) | — |
| Other Components | |
| D-Glucose | 2000.00 |
| HEPES | — |
| Lipoic Acid | — |
| Phenol Red | 10.00 |
| Sodium Pyruvate | — |
| Amino Acids | |
| L-Alanine | — |
| L-Arginine-HCl | 126.00 |
| L-Asparagine-H$_2$O | — |
| L-Aspartic Acid | — |
| L-Cystine-2HCl | 32.40 |
| L-Cystine-HCl—H$_2$O | — |
| L-Glutamic Acid | — |
| L-Glutamine | 292.00 |
| Glycine | — |
| L-Histidine | 31.00 |

TABLE 2-continued

| Component | Working pH range 7.0-7.4 mg/L |
|---|---|
| L-Histidine-HCl—H$_2$O | 42.00 |
| L-Isoleucine | 52.00 |
| L-Leucine | 52.00 |
| L-Lysine | 58.00 |
| L-Lysine-HCl | — |
| L-Methionine | 15.00 |
| L-Phenylalanine | 32.00 |
| L-Proline | — |
| L-Serine | — |
| L-Threonine | 48.00 |
| L-Tryptophan | 10.00 |
| L-Tyrosine-2Na—2H$_2$O | 52.00 |
| L-Valine | 46.00 |
| Vitamins | |
| L-Ascorbic Acid | — |
| Biotin | — |
| D-Ca pantothenate | 1.00 |
| Chlorine Chloride | 1.00 |
| Folic Acid | 1.00 |
| i-Inositol | 2.00 |
| Niacinamide | 1.00 |
| Pyridoxal-HCl | 1.00 |
| Riboflavin | 0.10 |
| Thiamine-HCl | 1.00 |
| Vitamin B12 | — |
| Deoxyribonucleosides | |
| 2' Deoxyadenosine | — |
| 2' Deoxyxytidine-HCl | — |
| 2' Deoxyguanosine | — |
| Thymidine | — |
| Ribonucleosides | |
| Adenosine | — |
| Cytidine | — |
| Guanosine | — |
| Uridine | — |

General Techniques for Culturing

General methods in molecular genetics and genetic engineering are described in the current editions of Sambrook et al. [84], Miller & Calm eds. [85], and F. M. Ausubel et al. eds. [86]. Cell biology, protein chemistry, and antibody techniques can be found in J. E. Colligan et al. eds. [87], J. S. Bonifacino et al., [88], and J. E. Colligan et al. eds. [89]. Reagents, cloning vectors, and kits for genetic manipulation referred to in this disclosure are available from commercial vendors such as BioRad (Hercules, Calif.), Stratagene (La Jolla, Calif.), Invitrogen Corporation (Carlsbad, Calif.), ClonTech (Mountain View, Calif.), and Sigma-Aldrich Co (St. Louis, Mo.).

Cell culture methods are described generally in Freshney ed, [90], M. A. Harrison & I. F. Rae [91], and K. Turksen ed. [92]. Cell culture supplies and reagents are available from commercial vendors such as Gibco/BRL (Gaithersburg, Md.), Nalgene-Nunc International (Rochester, N.Y.), Sigma Chemical Co. (St. Louis, Mo.), Hyclone (Logan, Utah), Chemicon International (Temecula, Calif.) and ICN Biomedicals (Costa Mesa, Calif.).

The demethylated cells can be grown on the plate in addition to the feeder cells. Alternatively, the feeder cells can be first grown to confluence and then mitotically inactivated (e.g., by irradiation) to prevent further growth. Alternatively the demethylated cells can be grown without feeder layer cells. Such an approach has the advantage of simplifying the management of the cell culture as the growth of only one set of cells, the demethylated cells, need only be monitored.

Culturing the Established Demethylated Cells: Once established, the demethylated cells can be cultured under the above-described conditioned medium using a variety of techniques. In one example, a container holds feeder cells in a non-conditioned medium. A matrix of lysed feeder cells is prepared using standard methods. The demethylated cells to be cultured are then added atop the matrix along with the conditioned medium. Alternatively, the demethylated cells can be grown on living feeder cells using methods known in the art. The growth of the demethylated cells is then monitored to determine the degree to which the cultured cells have become differentiated. A marker for alkaline phosphatase can be used to ascertain which cells have differentiated. When a sufficient number of cells have differentiated, or when the culture has grown to confluence, at least a portion of the undifferentiated cells can be passaged. The determination to passage the cells and the techniques for accomplishing such passaging can be performed using standard techniques well known in the art.

Dedifferentiating Somatic Cells in Culture: Cells are grown in custom-designed growth media deficient in one or more methyl donors or coenzymes (folate, betaine, choline, Vitamin B6, Vitamin B12 and methionine), or containing increased amounts of homocysteine or SAH. Formulations are based on Chemicon International Specialty Media (Phillipsburg, N.J.) or American Type Culture Collection (ATCC)-recommended media.

The formula deficiencies or supplements are shown in Table 3 as follows:

TABLE 3

| | Medium | | |
|---|---|---|---|
| | Most Preferable | Preferable [M] | Acceptable |
| Folate | 0 | 0-2.26 × 10$^{-5}$ | 0-4.53 × 10$^{-4}$ |
| Betaine | 0 | 0-8.53 × 10$^{-5}$ | 0-1.71 × 10$^{-3}$ |
| Choline | 0 | 0-3.38 × 10$^{-5}$ | 0-6.76 × 10$^{-4}$ |
| VitaminB$_6$ | 0 | 0-8.10 × 10$^{-9}$ | 0-1.62 × 10$^{-7}$ |
| VitaminB$_{12}$ | 0 | 0-1.23 × 10$^{-9}$ | 2.46 × 10$^{-8}$ |
| Methionine | 0 | 0-3.35 × 10$^{-4}$ | 6.67 × 10$^{-3}$ |
| Homocysteine | 0.0005 | 0.0001-0.001 | 0.00001-0.002 |
| SAH | 0.0005 | 0.0001-0.001 | 0.00001-0.002 |

As an example, the culture medium can be supplemented with 10% fetal bovine serum, 1% penicillin-streptomycin and 0.1% fungizone. Dialyzed fetal bovine serum (Invitrogen) is added to the folate deficient medium to eliminate folic acid in the serum. Cells are maintained at 37° C. in 95% humidity and 5% CO$_2$. Media is changed every 3-4. days, and cells are passaged at ~90% confluency repeatedly for up to 6 weeks. Endpoints include reduced cytosine methylation levels, reduced SAM:SAH ratios, and increased GNMT expression, activity and protein abundance.

To inhibit Dnmt activity and cytosine methylation, cells are grown in the following media:

(a) media treated with Dnmt1, 2, 3a, and/or 3b siRNA (Dharmacon, Inc.);

(b) media treated with RG108 (Analytical Systems Laboratory, LSU School of Veterinary Medicine);

(c) media treated with 5-AzadCyd (Sigma).

A brief description of siRNA transfection according to manufacturer's protocol is provided below.

To stimulate GNMT synthesis and activity, cells are grown in media treated with ATRA (Sigma). To protect ATRA from light exposure, the procedures are performed in subdued lighting and treatment flasks are wrapped in foil.

To inhibit histone deacetylation and induce demethylation, cells are grown in media treated with TSA and/or VPA (Sigma). Treatment concentrations are listed, but are not limited to, the conditions illustrated in Table 4 as follows:

TABLE 4

|  | Medium | | |
| --- | --- | --- | --- |
|  | Most Preferable | Preferable [µM] | Acceptable |
| Dnmt siRNA[a] | 0.05 | 0.01-0.1 | 0.001-0.2 |
| RG108[b] | 20 | 10-100 | 1-200 |
| AzadCyd[c] | 0.25 | 0.1-0.5 | 0.01-1.0 |
| ATRA[d] | 0.05 | 0.01-0.1 | 0.01-200 |
| TSA[e] | 0.30 | 0.1-3.0 | 0.01-300 |
| VPA[f] | $20 \times 10^3$ | $1-40 \times 10^3$ | $0.1-200 \times 10^3$ |

[a]Manufacturer recommendations of [100 nM] for 75% gene knockdown; 20-40% CpG island demethylation with [40 nM] Dnmt1 and/or 3b siRNA [133]; 79% gene knockdown and ~50% global genomic demethylation with [200 nM] Dnmt3b siRNA in NuPotential's preliminary studies.
[b]20% demethylation with [100 µM] RG108 [134].
[c]40% demethylation with [0.5 µM] AzadCyd [134].
[d]~25% demethylation with [100 nM] ATRA in our preliminary studies.
[e]5% demethylation with [0.2 µM] TSA [135].
[f]4.8% demethylation with [20 mM] VPA [135].

Cells are maintained at 37° C. in 95% humidity and 5% $CO_2$. Media is changed every 3-4 days with fresh treatment, and cells are passaged at ~90% confluency repeatedly for up to 6 weeks; see Dnmt siRNA transfection methods below for exception. Cell viability/cytotoxicity and growth rates are determined by relative cell counts. Endpoints include reduced cytosine methylation levels, reduced SAM:SAH ratios, increased GNMT expression, activity and protein abundance, and decreased Dnmt expression.

Dnmt siRNA transfection: At approximately 70-80% confluency, cells are transfected in growth media containing DharmaFECT (Dharmacon, Inc.) transfection reagent, Dnmt1, 2, 3a, and/or 3b siRNA (Dharmacon, Inc.), cyclophillin b siRNA (positive control siRNA), or *drosophila* non-targeting siRNA (negative control siRNA); Dnmt2 has not been determined to be functional and may serve as an additional control. Transfection is carried out according to manufacturer's protocol. Cells are incubated in transfection media for 48 hours. As per manufacturer's recommendation, if cell toxicity is observed after 24 hours, transfection media is replaced with growth media and incubation is continued for an additional 24 hours; wells exhibiting 80% viability after 48 hour incubation are used for differentiation.

Alternative Embodiments

The invention also is directed to development of a new assay based on use of reporter genes such as beta galactamase, luciferase, beta glucosidase, or others that provide the capability of monitoring the impact of GNMT expression and/or activity on demethylation and restoration of cell differentiation potential.

The invention is further directed to development of a novel method of SCNT using dedifferentiated donor cells.

The invention also is directed to development of a novel method to derive embryonic stem cells from SCNT reconstructed units (embryos).

EXAMPLES

The following Examples are included solely to aid in a more complete understanding of the subject invention. The Examples do not limit the scope of the invention described herein in any fashion.

Example 1

Effects of RA on Bovine Somatic Cell Methylation

Bovine serial nuclear transfer donor somatic cells (a cell line that has never produced a successful live animal and which is characterized by low blastocyst development rates (<10%, P<0.001) and low pregnancy initiation rates (<1%, P<0.05)) were cultured in T-75 flasks until confluent in growth media (CON), or growth media treated with DMSO, or ATRA (DMSO vehicle); 10 nM, 50 nM, and 100 nM ATRA concentrations were used. Following AMA treatment, the cells were collected and DNA from the cells was isolated. The DNA was then completely digested into single nucleotides for reverse-phase HPLC. Reverse-phase HPLC was performed as described by Cezar et al. [76] to measure the relative levels of methylated cytosine residues.

As illustrated in FIG. 1, HPLC revealed a 25% reduction in relative methylated cytosine in those cells cultured in 100 nM ATRA-treated media compared to CON. Those treated with DMSO or 10-50 nM ATRA exhibited an 8-10% reduction in methylated cytosine compared to CON. These results indicate that ATRA can reduce methylation status, in vitro, even in cells resistant to reprogramming, such as those obtained through serial nuclear transfer.

Figure 2:
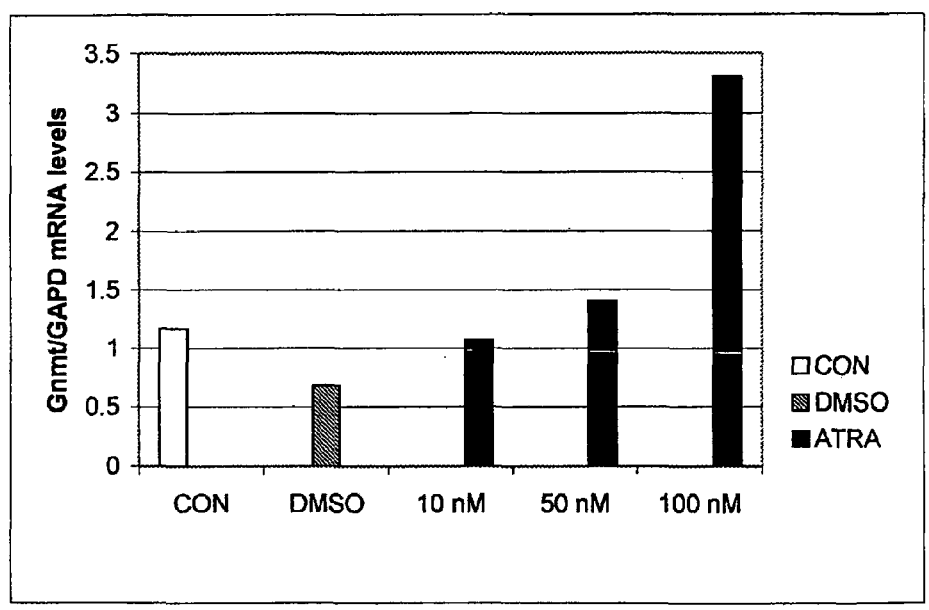
FIG. 2 is a graph illustrating the level of GNMT gene expression (as measured by real time PCR) in bovine serial nuclear transfer donor somatic cells after growth to confluence in growth media alone (CON), growth media treated with DMSO (DMSO), and growth media treated with all-trans retinoic acid (ATRA). See Example 1.

As illustrated in FIG. 2, real-time RT-PCR analysis demonstrated upregulation of the gene encoding glycine-N-methyltransferase (GNMT), the key enzyme regulating the SAM:SAH ratio and cellular methylation potential. (The results are depicted as the ratio of GNMT to glyceraldehyde-3-phosphate dehydrogenase (GAPD). The GAPD expression level is used to normalize the expression of the GNMT to a known marker.) Note that the upregulation of GNMT as shown in FIG. 2 happens simultaneously with the decreased DNA methylation shown in FIG. 1, Moreover, RT-PCR confirmed upregulation and strong expression of Oct4, the most diagnostic mammalian stem cell/pluripotency marker, as well as Sox2 and nanog (data not shown). The RT-PCR experiments were performed using a commercially available kit and following the manufacturer's instructions (TAQMAN-brand RT-PCR assays, Applied Biosystems, Foster City, Calif.) Others have demonstrated that demethylation of Oct4 is a requirement for efficient reprogramming of mice somatic nuclei [20].

These data indicate that exposure to ATRA increases expression of GNMT and likely activity of the GNMT enzyme, resulting in global demethylation (including demethylation of the Oct4 promoter and subsequent expression). Decreased DNA methylation is consistent with dedifferentiation, while increased expression of Oct4 is consistent with restoration of differentiation potential. To our knowledge, this is the first demonstration of a stem cell marker being induced in a mammalian somatic cell by altering single-carbon metabolism. The results are significant because they show that a mammalian cell can be induced to express a marker normally found only in undifferentiated stem cells, thus indicating that the cell can be reprogrammed to differentiate into a distinct cell type.

Example 2

Effects of RA and Adipogenic Induction Cocktail on Bovine Somatic Cells

To determine whether differentiation potential was restored, bovine somatic cells were cultured in T-75 flasks until confluent in CON, DMSO, or ATRA media (same RA as in Example 1). Following ATRA treatment, cells were collected for RNA isolation or transferred to 6-well plates and cultured in an adipogenic induction cocktail that included DMEM, FBS, insulin, IBMX and dexamethasone. The IBMX was removed and TZD was added 48 hours later. Cells remained in the induction media for 11-12 days, then were either oil red-O-stained (Aldrich, Milwaukee, Wis.) to ascertain the presence of lipid droplets, or collected for RNA isolation. RNA was reverse-transcribed to cDNA for RT-PCR for stem cell markers (Oct 4, Sox2, Nanog, AP) and adipogenic markers (PPARγ, LPL, FAS), or used directly in one-step quantitative real-time RT-PCR for GNMT. Glyceraldehyde-3-phosphate dehydrogenase (GAPDH) was used as a normalizing/housekeeping gene.

Figure 3A:
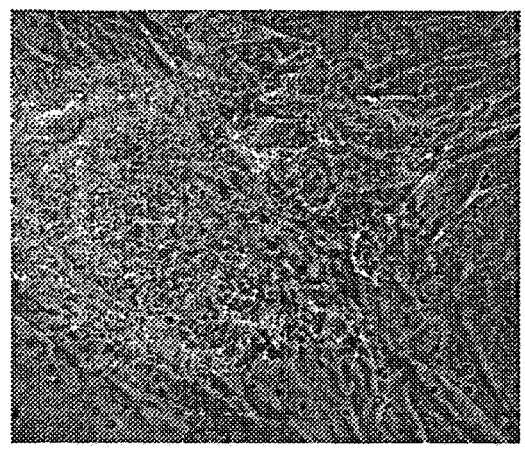
FIGS. 3A and 3B are photographs illustrating bovine cells treated as described in Example 2.
Figure 3B:
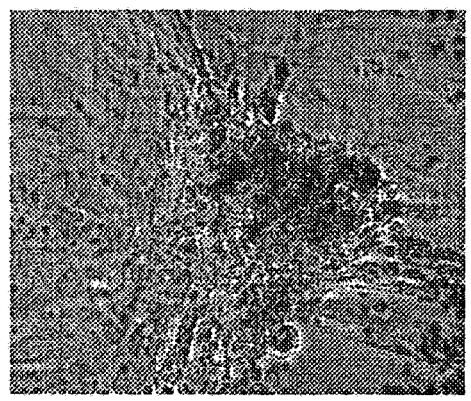

As illustrated in FIG. 3A, during exposure to ATRA, significant morphological changes were observed, including development of structures that were remarkably similar to embryoid bodies. As illustrated in FIG. 3B by the arrow, positive oil red-O staining was also observed after induction, indicating the presence of lipid. Gene expression analyses by PCR revealed induction of PPARγ, a known marker of adipocyte differentiation (data not shown). These results are significant because they suggest that somatic cells can be induced to re-differentiate into other cell types.

Example 3

Effects of RA and Adipogenic Induction Cocktail on Primary Hepatocytes

Primary rat hepatocytes were grown in media treated with 50-200 nM ATRA. Following treatment, cells were cultured under the same comparative conditions as described above for the bovine somatic cells, except an adipogenic induction cocktail (as described in EXAMPLE 2) was added to the T-75 flasks. Morphological changes were observed during ATRA treatment, and within 48 hours after initial exposure to induction media, these changes became pronounced. By day 4 of exposure to adipogenic induction media, these morphological changes were accompanied by the beginnings of spheroid body development and distinct proliferation of cells as evidenced by confluency, a state not reached in control cells. These observations suggest that these primary hepatocytes that are terminally differentiated re-entered the cell cycle following ATRA treatment and exposure to adipogenic induction media in culture and proliferated significantly following the treatments.

Example 4

Effects of RA and Osteogenic Induction Cocktail on Murine Somatic Cells

Figure 4A:
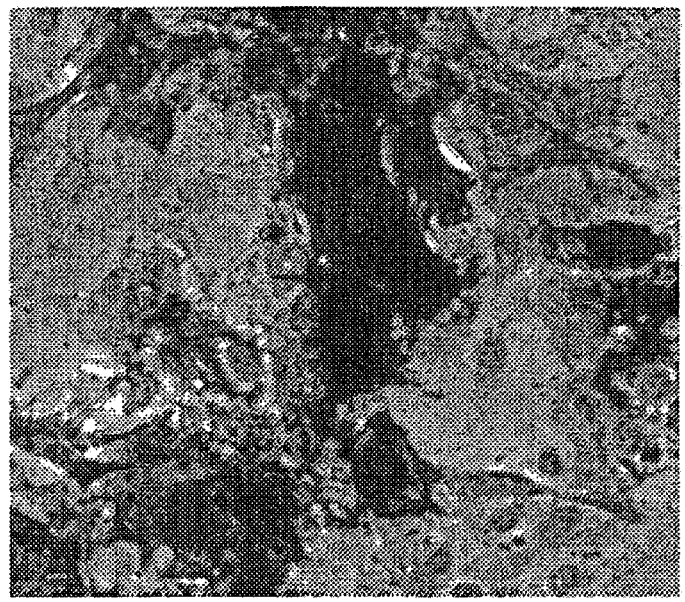
FIGS. 4A and 4B are photographs showing murine 3T3 L1 cells treated with ATRA followed by osteogenic induction media, as described in Example 4.
Figure 4B:
Figure 5:
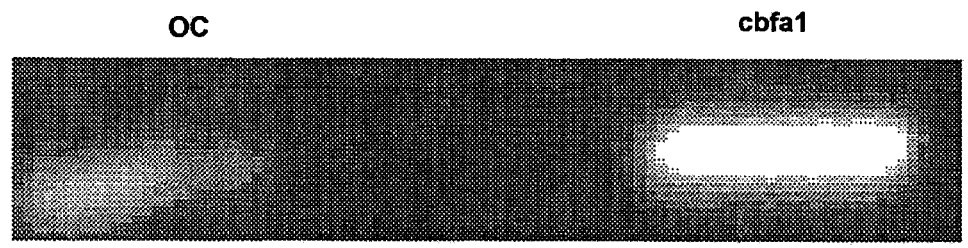
FIG. 5 is a photograph of a gel illustrating gene expression (by RT-PCR) for osteocalcin and cbfa1, osteoblast-specific markers, in murine 3T3 L1 cells treated with ATRA followed by osteogenic induction media. See Example 4.

3T3 L1 cells were grown in media treated with 50-200 nM ATRA. Following ATRA treatment, cells were transferred to 6-well plates and exposed to osteogenic induction media containing DMEM, FBS, ascorbic acid 2-phosphate, dexamethasone, beta glycerophosphate, and vitamin D for 21 days. As illustrated in FIG. 4A and FIG. 4B, following osteogenic induction, positive staining for osteoblast-like cells (FIG. 4A) and calcium phosphate mineralization (FIG. 4B) was observed with alkaline phosphatase and alizarin staining, respectively. As illustrated in FIG. 5, RT-PCR revealed induction of osteocalcin and cbfa1, known markers of osteoblast-specific differentiation.

Example 5

Production of Cell Lines and Production of Cell Cultures that Produce Cells with Restored Differentiation Potential by Knocking Down DNA Methyltransferases 1, 3A, and/or 3B using Interfering RNA Technology Knocking down DNA methyltransferases 1, 3a, and/or 3b using interfering RNA technology results in reduced levels of DNA methylation. By modifying the culture media to incorporate siRNA technology, selective gene expression suppression can be accomplished. The methodology for achieving this impact-including foundation media, specific treatments and modification to that media, and methods of confirming knock down potential is described below.

Altering single-carbon metabolism and/or inhibiting DNMT activity induces global DNA demethylation which can restore differentiation potential. De-differentiated cell lines capable of re-differentiating into multiple lineages can be produced by global epigenetic reprogramming. Preliminary studies designed to analyze the impact of DNMT gene knockdown using siRNA technology on global DNA demethylation in a bovine donor cell line for SCNT and a murine fibroblast cell line demonstrate how this is accomplished.

Example 5.1

Effects of DNA Methyltransferase 1 siRNA Transfection on Bovine Somatic Donor Cell Methylation and Developmental Potential Bovine oocytes aspirated from abattoir ovaries were matured overnight in maturation medium (medium 199; Biowhittaker) supplemented with luteinizing hormone (10 IU/ml; Sigma), estradiol (1 mg/ml; Sigma), and FBS (10%; tlyclone, Logan, Utah) at 38.5° C. in a humidified 5% $CO_2$ incubator. Bovine nuclear transfer was performed as described by Forsberg et al. [131]. A human siRNA to Dnmt1 used by Robert et al. [140]) was ordered from Dharmacon RNA Technologies (Lafayette, Colo.). The sequence was as follows: AAGCAUGAGCACCGUUCUCC.dT.dT. (SEQ. ID. NO: 1) This was duplexed and desalted as per manufacturer's instructions. Transfection of siRNA occurred according to LIPOFECTIN manufacturer protocol Briefly, 2 μM siRNA in 1× Universal buffer was mixed with LIPOFECTIN (Invitrogen) transfection reagent with serum free growth medium (Opti-MEM; Invitrogen). (Invitrogen) and Robert et al [140]. Prior to transfection, culture medium was removed from cells that were ~40-60% confluent and 3 ml transfection reagent solution was added, with final transfection concentrations of 200 nM siRNA and 0.6% LIPOFECTIN transfection reagent.

The cells were incubated for 24 hours at 37° C. and washed with AmnioMAX-brand media containing serum (Invitrogen). Cells were transfected twice prior to analysis. Control and Test samples were generated simultaneously and include:
1. Cells treated with media alone.
2. Cells treated with transfection reagent (LIPOFECTIN) alone.

3. Cells treated with control siRNA (Lamin A/C; Dharmacon).
4. Cells treated with Test siRNA (Dnmt1; Dharmacon)

Figure 6B:
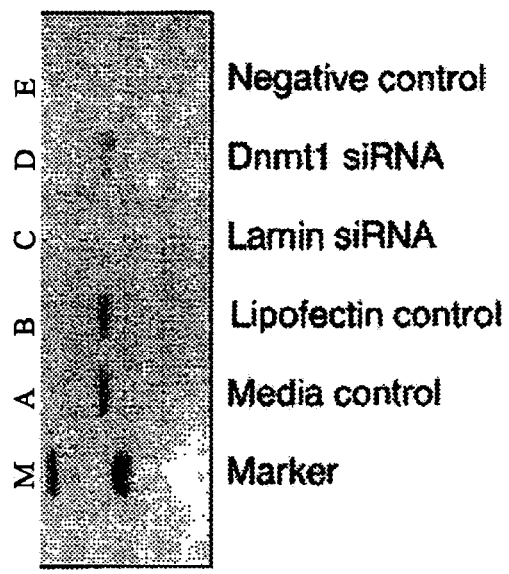
FIGS. 6A and 6B are photographs of gels illustrating the knock down of the Dnmt1 gene by siRNA, as described in Example 5.
Figure 6A:
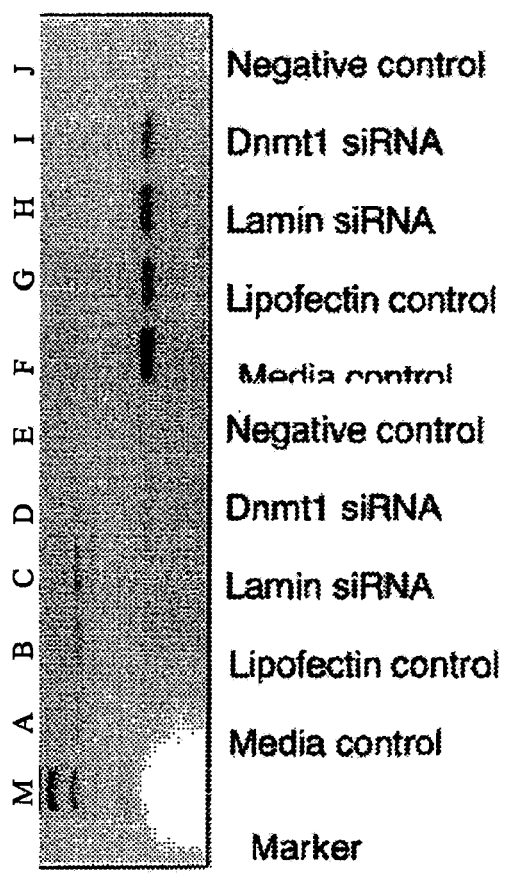
Figure 6C:
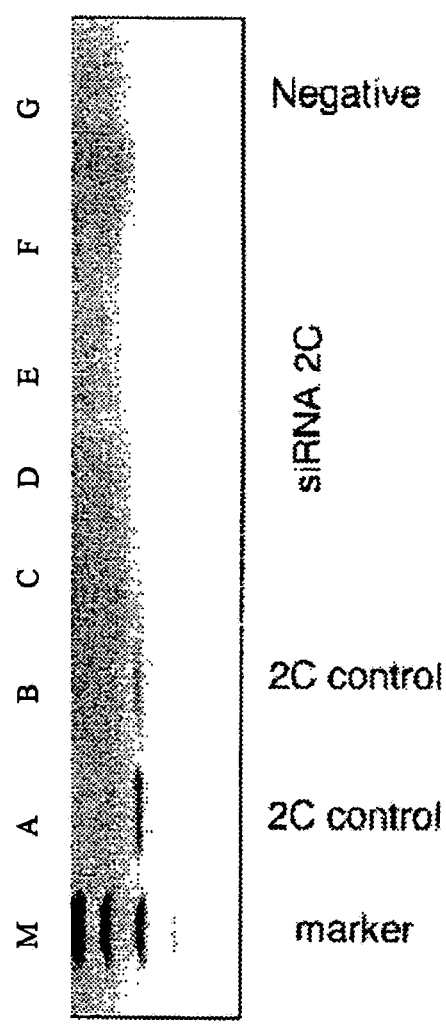
FIG. 6C is a photograph of a gel showing that the knock down of Dnmt1 as shown in FIG. 6A persisted through at least the two-cell stage. See Example 5.

The following figures and legends summarize these studies. FIG. 6A and FIG. 6B illustrate the knockdown of Dnmt1 by siRNA. Dnmt1 was efficiently knocked down after siRNA treatment of bovine donor cells for SCNT (FIG. 6A, Lane D) while actin expression was not affected (FIG. 6A, Lanes G-I). In contrast, exposure to lamin siRNA knocked down lamin expression, (FIG. 6B, lane C) but not Dnmt1 (FIG. 6A, lane C). HPLC analysis confirmed an approximately 40% decrease in global methylation levels in cells treated with Dnmt 1 siRNA, and the cells were subsequently used for SCNT. FIG. 6C illustrates that knockdown of Dnmt1 persisted through at least the 2 cell stage (lanes C-F) when compared to controls (lanes A & B), and blastocyst development rates were significantly higher when compared to controls (50% vs 21%, p<0.05).

Example 5.2

Effects of DNA Methyltransferase 3b siRNA Transfection on Murine Somatic Cell Methylation NIH3T3 cells were transfected with 200 nM murine Dnmt3b siRNA (Dharmacon RNA Technologies, Lafayette, Colo.). Pooled siRNA sequences are as follows: GCAAUGAUCUCUCUAACGU (SEQ. ID. NO: 2); GGAAUGCGCUGGGUACAGU (SEQ. ID. NO: 3); UAAUCUGGCUACCUUCAAU (SEQ. ID. NO: 4); GCAAAGGUUUAUAUGAGGG (SEQ. ID. NO: 5). The transfection protocol was optimized in our lab essentially as described by the manufacturer. Briefly, 2 µM siRNA in 1×siRNA buffer was mixed with DharmaFECT transfection reagent with serum free growth medium (DMEM; Hyclone, Logan, Utah). Prior to transfection, culture medium was removed from cells that were ~70-80% confluent and transfection reagent solution was added to cover the surface. Final transfection concentrations were 200 nM siRNA and 0.6% DharmaFECT transfection reagent in a 2 ml total volume per well of E-well plates.

Cells were incubated at 37° C. in 5% CO$_2$ for 24-48 hours. All experiments included the following Control and Test samples in triplicate:
1. Untreated cells (media alone)
2. Mock transfection (no siRNA; DhannaFECT only)
3. Positive control siRNA (cyclophillin b)
4. Negative control siRNA (drosophila non-targeting)
5. Test siRNA (Dnmt 3b)

Figure 7A:
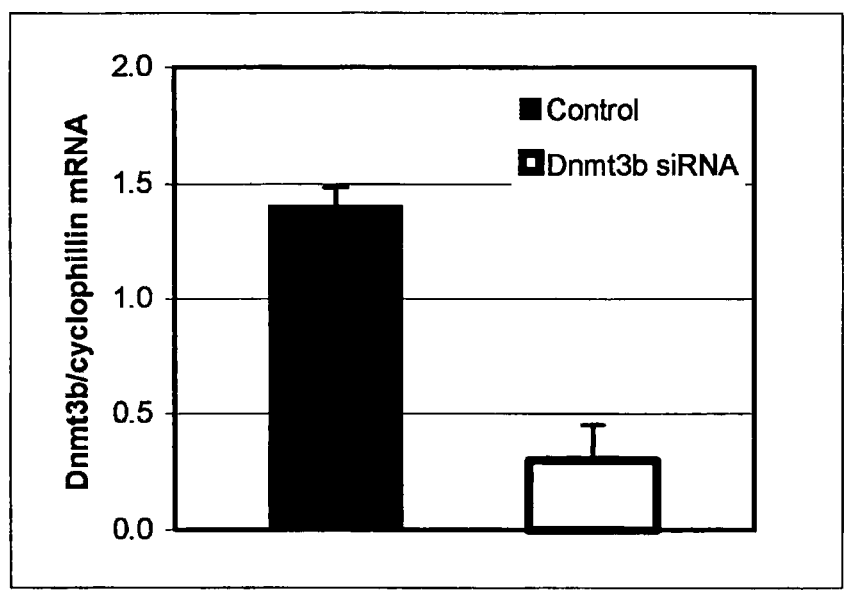
FIGS. 7A and 7B are graphs illustrating the effects of DNA methyltransferase 3b siRNA transfection on murine NIH3T3 somatic cell methylation, as described in Example 5.1.
Figure 7B:
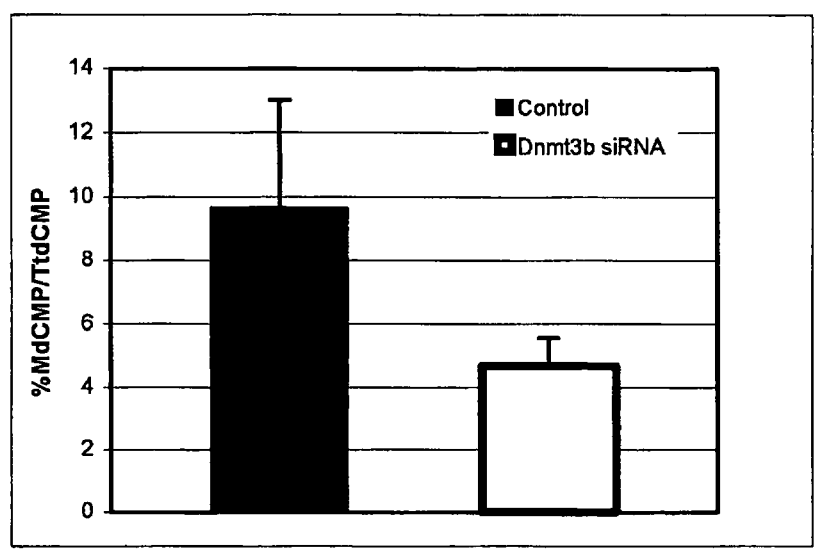

Dnmt3b mRNA expression was determined by real-time RT-PCR (using a TAQMAN-brand RT-PCR kit and following the manufacturer's instructions). The results are shown in FIG. 7A; n=2. Methylation levels were determined via HPLC. The results are shown in FIG. 7B; n=3.

As illustrated in FIG. 7A, real-time RT-PCR revealed a 79% decrease in Dnmt3b mRNA levels relative to cyclophillin b in cells transfected with Dnmt3b siRNA as compared to control cells. As illustrated in FIG. 7B, HPLC revealed a 52% reduction in methylated cytosine in cells transfected with Dnmt3b siRNA as compared to control cells. These data indicate that Dnmt3b gene knockdown can reduce methylation status, in vitro.

Example 6

New Media for DNA Methyltransferase siRNA Transfection in Human and Murine Somatic Cells Additional human and murine Dnmt siRNAs have been purchased from Dharmacon (Lafayette, Colo.). Pooled siRNA sequences are as follows:

```
1. Human Dnmt1:
GGAAGAAGAGUUACUAUAG;      (SEQ. ID. NO: 6)
GAGCGGAGGUGUCCCAAUA;      (SEQ. ID. NO: 7)
GGACGACCCUGACCUCAAA       (SEQ. ID. NO: 8)
GAACGGUGCUCAUGCUUAC.      (SEQ. ID. NO: 9)

2. Human Dnmt3a:
GCACAAGGGUACCUACGGG;      (SEQ. ID. NO: 10)
CAAGAGAGCGGCUGGUGUA;      (SEQ. ID. NO: 11)
GCACUGAAAUGGAAAGGGU;      (SEQ. ID. NO: 12)
GAACUGCUUUCUGGAGUGU.      (SEQ. ID. NO: 13)

3. Human Dnmt3b:
GAAAGUACGUCGCUUCUGA;      (SEQ. ID. NO: 14)
ACAAAUGGCUUCAGAUGUU;      (SEQ. ID. NO: 15)
GCUCUUACCUUACCAUCGA;      (SEQ. ID. NO: 16)
UUUACCACCUGCUGAAUUA.      (SEQ. ID. NO: 17)

4. Murine Dnmt1: 1-
GGAAAGAGAUGGCUUAACA;      (SEQ. ID. NO: 18)
GCUGGGAGAUGGCGUCAUA;      (SEQ. ID. NO: 19)
GAUAAGAAACGCAGAGUUG;      (SEQ. ID. NO: 20)
GGUAGAGAGUUACGACGAA.      (SEQ. ID. NO: 21)

5. Murine Dnmt3a:
CGCGAUUUCUUGAGUCUAA;      (SEQ. ID. NO: 22)
CGAAUUGUGUCUUGGUGGA;      (SEQ. ID. NO: 23)
AAACAUCGAGGACAUUUGU;      (SEQ. ID. NO: 24)
CAAGGGACUUUAUGAGGGU.      (SEQ. ID. NO: 25)
```

All protocols will be optimized in our lab essentially as described by the manufacturer. Briefly, 2 µM siRNA in 1×siRNA buffer is mixed with DharmaFECT transfection reagent with serum free growth medium (DMEM; Hyclone, Logan, Utah). Prior to transfection, culture medium will be removed from cells that are ~70-80% confluent and transfection reagent solution will be added to cover the surface. Final transfection concentrations are 200 nM siRNA and 0.6% DharmaFECT transfection reagent in a 2 ml total volume per well of 6-well plates.

Cells will be incubated at 37° C. in 5% CO$_2$ for 24-48 hours. All experiments will include the following samples in triplicate: untreated cells, mock transfection (no siRNA, DharmaFECT only), positive control siRNA (cyclophillin b), negative control siRNA (drosophila non-targeting), and test siRNA.

Real time RT-PCR will be used to confirm gene knockdown. HPLC will be used to measure relative cytosine methylation levels.

Example 7

New Media that Knocks Down MTHFR and/or Cbs using Interfering RNA Technology

Knocking down MTHFR and/or Cbs using interfering RNA technology results in decreased SAM:SAH ratio and DNA methylation. Appropriate siRNAs are purchased commercially (Dharmacon RNA technologies, Lafayette, Colo.) and are duplexed and desalted according to manufacturer's instructions. Pooled human and murine siRNA sequences are as follows:

```
Human MTHFR:
AGUGAGAGCUCCAAAGAUA;      (SEQ. ID. NO: 26)
GAAGUGAGUUUGGUGACUA;      (SEQ. ID. NO: 27)
GACCAAAGAGUUACAUCUA;      (SEQ. ID. NO: 28)
GCAAGUGUCUUUGAAGUCU.      (SEQ. ID. NO: 29)

Human Cbs:
AGACGGAGCAGACAACCUA;      (SEQ. ID. NO: 30)
CACCACCGCUGAUGAGAUC;      (SEQ. ID. NO: 31)
```

-continued

```
GGACGGUGGUGGACAAGUG;      (SEQ. ID. NO: 32)
GGAAGAAGUUCGGCCUGAA.      (SEQ. ID. NO: 33)

Murine MTHFR:
CGCCAUGGCUACAGAGUAA;      (SEQ. ID. NO: 34)
GCGGAAACCAGCCUGAUGA;      (SEQ. ID. NO: 35)
CAGAAGGCCUACCUCGAAU;      (SEQ. ID. NO: 36)
CAUACGAGCUGCGGGUCAA.      (SEQ. ID. NO: 37)

Murine Cbs:
GCAAACAGCCUAUGAGGUG;      (SEQ. ID. NO: 38)
GCAAAGUCCUCUACAAGCA;      (SEQ. ID. NO: 39)
GAUCGAAGAUGCUGAGCGA;      (SEQ. ID. NO: 40)
CAACCCUUUGGCACACUA.       (SEQ. ID. NO: 41)
```

Positive and negative siRNAs are purchased from Dharmacon and used directly in transfections.

All protocols are optimized essentially as described by the manufacturer. Briefly, 2 μM siRNA in 1×siRNA buffer is mixed with DharmaFECT transfection reagent with serum free growth medium (DMEM; Hyclone, Logan, Utah). Prior to transfection, culture medium is removed from cells that are ±70-80% confluent and transfection reagent solution is added to cover the surface. Final transfection concentrations are 200 nM siRNA and 0.6% DharmaFECT transfection reagent in a 2 ml total volume per well of 6-well plates.

Cells are incubated at 37° C. in 5% CO2 for 24-48 hours. All experiments will include the following samples in triplicate: untreated cells, mock transfection (no siRNA, DharmaFECT only), positive control siRNA (cyclophillin b), negative control siRNA (drosophila non-targeting), and test siRNA.

Real time RT-PCR is used to confirm gene knockdown. HPLC is used to measure relative cytosine methylation levels.

Example 8

New Media that Increases the Transcription, Protein Expression and Activity of GNMT Increasing the transcription, protein expression and activity of GNMT results in decreased SAM:SAH ratio and DNA methylation. This involves identification of compounds, extracts, molecules that have similar effects as ATRA such as increasing GNMT activity, and/or decreasing SAM:SAH ratio.

Depleting methyl donors in vitro results in decreased SAM:SAH ratio and DNA methylation. The medias are custom designed and deficient in one or more methyl donors or coenzymes (folate, betaine, choline, Vitamin B6, Vitamin B12 and methionine and/or others); or, have increased amounts of homocysteine; or combinations of deficient methyl donors/coenzymes and/or increased levels of homocysteine. The formulations are based on HyClone's 1640 medium (HyClone, Logan, Utah) with modifications as shown in Table 5:

TABLE 5

| Component: | | Experimental Medium g/L | Control Medium g/L |
|---|---|---|---|
| Medium 1: | Betaine | 0 | 0.03 |
| Medium 2: | Choline | 0 | 0.03 |
| Medium 3: | Vitamin $B_6$ | 0 | 0.000005 |
| Medium 4: | Vitamin $B_{12}$ | 0 | 0.000005 |
| Medium 5: | Methionine | 0 | 0.15 |
| Medium 6: | Folate | 0 | 0.03 |

Example 9

Media that Increase Levels of Homocysteine In Vitro

Increasing levels of homocysteine in vitro results in decreased SAM:SAH ratio and DNA methylation. The medias are custom designed to contain increased amounts of homocysteine; or combinations of deficient methyl donors/coenzymes and/or increased levels of homocysteine. The formulations are based on HyClone's 1640 medium with modifications as shown in Table 6:

TABLE 6

| Component: | | Experimental Medium g/L | Control Medium g/L |
|---|---|---|---|
| Medium 6: | Homocysteine | 0.0625 | 0 |
| Medium 7: | Folate | 0 | 0.03 |
|  | Homocysteine | 0.0625 | 0 |
| Medium 8: | Betaine | 0 | 0.03 |
|  | Homocysteine | 0.0625 | 0 |
| Medium 9: | Choline | 0 | 0.03 |
|  | Homocysteine | 0.0625 | 0 |
| Medium 10: | Vitamin $B_6$ | 0 | 0.03 |
|  | Homocysteine | 0.0625 | 0 |
| Medium 11: | Vitamin $B_{12}$ | 0 | 0.03 |
|  | Homocysteine | 0.0625 | 0 |

Culturing cells in defined media having reduced or depleted levels of a specific methyl donor, or multiple methyl donors, or containing increased levels of homocysteine, or increased levels of homocysteine in combination with reduced or depleted levels of a specific methyl donor, or methyl donors, results in decreased SAM:SAH ratio and DNA methylation.

Example 10

High Throughput Assay using GNMT Promoter

Factors that increase expression of, and/or activate GNMT, are likely to down regulate DNA methyltransferases and reduce global methylation levels. A β-lactamase-based assay (and/or other assays described below) are developed to identify inducers (and suppressors) of GNMT expression by induction of GNMT transcription.

β-lactamase assay (Invitrogen) is used to develop cell based assays that can be used to identify drugs, molecules and extracts that induce DNA demethylation through the single-carbon metabolism pathway and to identify drugs, molecules and extracts that induce redifferentiation of in vitro restored pluri- and multipotent cell lines. The initial objective is to develop a cell based assay that can be used to screen for drugs, molecules and extracts that induce expression of GNMT.

The basis of this assay will be the GENEBLAZER technology (Invitrogen), a gene reporter system based on a membrane permeant fluorescence resonance energy transfer (FRET)-based substrate (CCF2-AM) that provides viable cell staining, compatibility with fluorescence-activated cell sorting, ratiometric read-out and an optimized platform for high throughput screening. Excitation of CCF2 at 405 nm results in a blue/green emission due to the absence of FRET, respectively, in the CCF2 substrate molecule. The cell permeable CCF2-AM consists of 2 fluorophores, 7-hydroxycoumarin and fluorescein, linked by a cephalosporin core.

Excitation of coumarin at 405 nm results in FRET to the fluorescein moiety, which emits green fluorescence light at 530 nm. β-lactamase cleaves the β-lactam moiety within the cephalosporin core of the CCF2-AM substrate molecule into two separate fluorophores, resulting in FRET disruption.

Excitation of the cells at 405 nm results in blue fluorescence emission by coumarin, detected at 460 nm. The presence of β-lactamase in the cells causes a change from green to blue fluorescent cells. Thus, during FACS analysis cells with different emission characteristics can be collected.

A 1.8 kb DNA fragment that contains the 5' upstream region of human GNMT is PCR amplified from genomic DNA. The primers used are:

Pr4564: 5'-GGGGTACCAGCATCTT-3' (SEQ. ID. NO: 42) and

Pr6391: 5'-GCGAGATCTCCTGCGCCGCGCCTGGCT-3' (SEQ. ID. NO: 43).

PCR conditions are as follows: 1.5 mM $MgCl_2$, 200 nm primers, 35 cycles consisting of an annealing step at 60° C. for 1 min, extension at 72° C. for 2 min and 35 cycles.

After amplification, SDS and EDTA are added to 0.1% and 5 mM, respectively. DNA is precipitated with 2.5 M ammonium acetate and 70% ethanol. The fragment is digested with KpnI and BglII and the fragment isolated by elution from agarose after gel electrophoresis. The fragment is ligated into vector p7-blaM carrying the β-lactamase M coding sequence (blaM) gene. The construct is transfected into CHO-K1 cells using Lipofectamine 2000 brand reagent (Invitrogen) as transfection reagent. Vector without insert is transfected as a negative control. Stable cells are selected by resistance to Zeocin. Cells are grown in phenol-red free MEM-α medium with 10% charcoal-treated serum, pen/strep and 10 mM HEPES buffer.

Clones with low β-lactamase expression are selected by FACS analysis. Cells are trypsinized and washed twice with FACS buffer [phosphate-buffered saline (PBS), 5% charcoal treated FBS] and loaded at a concentration of $1 \times 10^6$ cells/ml with appropriate GENEBLAZER technology, cell permeable FRET-based substrate (CCFs-AM) in the dark with mild shaking for 1 hour.

Cells are harvested by centrifugation and resuspended in FACS buffer at the same cell concentration. Cells are sorted using a Becton-Dickenson FACStarplus cell sorter (Franklin Lakes, N.J.). An argon UV laser is used to excite cells loaded with substrate. Clones with responding green fluoroescene are collected into 96-well plates containing growth media with 200 g/ml Zeocin and grown to a final cell population of $6 \times 106$. Stable cell lines are tested for inducibility by treatment with ATRA.

Prior experiments have demonstrated a dose response of GNMT transcription to ATRA. This response is used as criteria for a successful assay. Specifically, an assay is considered successful when a 3 fold induction is detected by treatment with 100 nM ATRA and confirmed by real-time PCR. Clones with an ATRA inducible β-lactamase expression are identified and used for further development.

It is also within the scope of the present invention to utilize assays with similar applications using other reporter genes such as luceriferase, beta-galactosidase, or others.

It is understood that the invention is not confined to the particular construction and arrangement of parts herein illustrated and described, but embraces such modified forms thereof as come within the scope of the claims following the Bibliography.

BIBLIOGRAPHY

1. Balaghi M, Wagner C. DNA methylation in folate deficiency: use of CpG methylase. Biochm Biophys Res Commun. 1993; 193:1184-1190.
2. Alonso-Aperte E, Varela-Moreiras G. Brain folate and DNA methylation in rats fed a choline deficient diet or treated with low doses of methotrexate. Int J Vitamin Nutr Res. 1996; 66_232-236.
3. Jacob R A, Gretz D M, Taylor P C, et al. Moderate folate depletion increases plasma homocysteine and decreases lymphocyte DNA methylation in postmenopausal women. J. Nutr. 1998; 128:1204-1212.
4. Rampersaud G C, Kauwell G P, Hustson A D, Cerda J J, Bailey L B. Genomic DNA methylation decreases in response to moderate folate depletion in elderly women. Am J Clin Nutr. 2000; 72:998-1003.
5. Pufulete M, AI-Ghaniem R, Leather A J, et al. Folate status, genomic DNA hypomethylation, a risk of colorectal adenoma and cancer: a case control study. Gastroenterology. 2003; 124:1240-1248.
6. Fowler B M, Giulano A R, Piyathilake C, Nour M, Hatch K. Hypomethylation in cervical tissue: is there a correlation with folate status? Cancer Epidemiol Biomarkers Prey. 1998; 7:901-906.
7. Fang J Y, Xiao S D, Zhu S S, Yuan J M Qiu D K, Jiang S J. Relationship of plasma folic acid and status of DNA methylation in human gastric cancer. J. Gastroenterol. 1997; 32:171-175.
8. Friso S, Choi S W, Girelli D, et al. A common mutation in the 5,10-methylenetetrahydrofolate reductase gene affects genomic DNA methylation through and interaction with folate status. Proc Natl Acad Sci USA. 2002; 99:5606-5611.
9. Cravo M, Fidalgo P, Pereira A D et al. DNA methylation as an intermediate in colorectal cancer: modulation by folic acid supplementation.
10. Kim Y I, Baik H W, Fawaz K, et al. Effects of folate supplementation on two provisional molecular markers of colon cancer: a prospective, randomized trial. Am J. Gastroneterol. 2001; 96:184-195.
11. Ingrosso D, Cimmino A, Perna A F, et al. Folate treatment and unbalanced methylation and changes of allelic expression induced by hyperhomocysteinaemia in patients with uraemia. Lancet. 2003; 361:1693-1699.
12. Duthie S J, Narayanan S, Slum S, Pirie L, Brand G M. Folate deficiency in vitro induces uracil misincorporation and DNA hypomethylation and inhibits DNA excision repair in immortalized normal human colon epithelial cells. Nutr Cancder. 2000; 37:245-251.
13. Carlson L L, Page A W, Bestor T H. Properties and localization of DNA methyltransferase in pre-implantation mouse embryos: implications for genomic imprinting. Genes Dev. 1992; 6:2536-2541.
14. Chen T, Ueda Y, Dodge J E, Wang J, Li E. Establishment and maintenance of genomic methylation patterns in mouse embryonic stem cells by Dnmt3a and Dnmt3b. Mol Cell Biol. 2003; 23:5594-5604.
15. Lei H, Oh S P, Okano M, Jutterman R, Goss K A, Jaensisch R, Li E. De novo DNA cystosine methyltransferase activities in mouse embryonic stem cells. Development. 1996; 122:3195-3205.
16. Mayer W, Niveleau A, Walter R, Funele R, Haaf T. Demethylation of the zygotic paternal genome. Nature. 2000; 403:501-502.
17. Okano M, Bell D W, Haber D A, Li E. DNA methyltransferases Dnmt3a and Dnmt3b are essential for de novo methylation and mammalian development. Cell. 1991; 99:247-257.
18. Panning B, Jaenisch R. DNA hypomethylation can activate Xist expression and silence X-linked genes. Genes Dev. 1996; 10:1991-2002.

19. Jackson M, Krassowska A, Gilbert N et al. Severe global DNA hypomethylation blocks differentiation and induces histone hypereacetylation in embryonic stem cells. Mol Cell Biol. 2004; 25:8862-8871.
20. Somonsson S, Gurdon J. DNA methylation is necessary for the epigenetic reprogramming of somatic cell nuclei. Nat Cell Bio. 2004; 6:984-990.
21. Bird A. DNA methylation patterns and epigenetic memory. Genes Dev. 2002; 16:6-21.
22. Li, E. Chromatin modification and epigenetic programming in mammalian development. Nat Rev Genet. 2002; 3:662-673.
23. Reik W, Dean W, Walter J. Epigenetic reprogramming in mammalian development. Science. 2001; 293:1089-1093.
24. Rideout W M, Eggan K, Jaenisch R. Nuclear cloning and epigenetic reprogramming of the genome. Science. 2001; 293:1093-1098.
25. Surani M A. Reprogramming of genome function through epigenetic inheritance. Nature. 2001; 414:122-128.
26. Feinberg A P, Tycko B. The history of cancer epigenetics. Nat Rev Cancer. 2004; 4:143-153.
27. Goodell M A. Stem cell plasticity: befuddled by the muddle. Curr Opin Hematol. 2003; 10:208-213.
28. Pomerantz J, Blau H M. Nuclear reprogramming: a key to stem cell function in regenerative medicine. Nat Cell Biol. 2004; 6:810-816.
29. Hsieh J, Gage F H. Epigenetic control of neural stem cell fate. Curr Opin Genet Dev. 2004; 14:461-469.
30. Dean W, Santos F, Reik W. Epigenetic programming in early mammalian development and following SCNT. Semin Cell Dev Biol. 2003; 14:93-100.
31. Jouneau A, Renard J P. Reprogramming in nuclear transfer. Curr Opin Genet Dev. 2003; 13:486-491.
32. Kang Y K, Lee K K, Han Y M. Reprogramming DNA methylation in the preimplantation stage: peeping with Dolly's eyes. Curr Opin Cell Biol. 2003; 15:290-295.
33. Hochedlinger K, Rideout W M, Kyba M et al., Nuclear transplantation, embryonic stem cells and the potential for cell therapy. Hematol J. S3. 2004; S114-S117.
34. Santos F, Hendrich B, Reik W, Dean W. Dynamic reprogramming of DNA methylation in the early mouse embryo. Dev Biol. 2002; 241:172-182.
35. Lane N, Dean W, Erhardt S, Hajkova P, Surani A, Walter J, Reik W. Resistance of IAP to methylation reprogramming may provide a mechanism for epigenetic inheritance in the mouse. Genesis. 2003; 35:88-93.
36. Adenot, P G, Mercier Y, Renard J P, Thompson E M. Differential H4 acetylation of paternal and maternal chromatin precedes DNA replication and differential transcriptional activity in pronuclei of 1-cell mouse embryos. Development. 1997; 124:4625-4625.
37. Lepikhov K, Walter J. Differential dynamics of histone H3 methylation at positions K4 and K9 in the mouse zygote. BMC Dev Biol. 2004; 4:12-16.
38. Erhardt S, Su H I, Schnieder R, Barton S, et al. Consequences of the depletion of zygotic and embryonic enhancer of zeste 2 during preimplantation mouse development. Development. 2003; 130:4235-4248.
39. Santos F, Peters A H, Otte A P, Reik W, Dean D. Dynamic chromatin modifications characterize the first cell cycle in mouse embryos. Dev Biol. 2005; 280:225-236.
40. Monk M, Boubelik M, Lehnert S. Temproal and regional changes in DNA methylation in the embryonic, extraembryonic and germ cell lineages during mouse embryo development. Development. 1987; 99:371-382.
41. Howlett S K, Reik W. Methylation levels of maternal and paternal geneomes during preimplantation development. Development. 1991; 113:119-127.
42. Bestor T R The DNA methyltransferases of mammals. Hum Mol. Genet. 2000; 9:2395-2402.
43. Howell C Y, Bestor T H, Ding F, Latham K E, et al. Genomic imprinting disrupted by a maternal effect mutation in the Dnmt1 gene. Cell. 2001; 104:829-838
44. Fujimori T, Kurotald Y, Miyazaki J, Nabeshima Y. Analysis of cell lineage in two- and four-cell mouse embryos. Development. 2003; 130:5113-5122.
45. Santos F, Zakhartchenko V, Stojkovic M et al., Epigenetic marking correlates with developmental potential in cloned bovine preimplantation embryos. Curr Biol. 2003; 13:1116-2111.
46. Zhang S, Kubot C, Yang L et al. Genomic imprinting of H19 in naturally reproduced and cloned cattle. Biol Reprod. 2004; 71:1540-1544.
47. Eggan K, Akutsu H Hochedlinger K et al. X-chromosome inactivation in cloned mouse embryos. Science. 2000; 290: 1578-1581.
48. Xue F, Tian X C, Du F, et al. Aberrant patterns of X chromosome inactivation in bovine clones. Nat. Genet. 2002; 31:216-220.
49. Humphreys D, Eggan K, Akutsu H et al. Epigenetic instability in ES cells and cloned mice. Science. 2001; 293:95-97.
50. Inoue K, Kohda T, Lee J, et al. Faithful expression of imprinted genes in cloned mice. Science. 2002; 295:297-297.
51. Mann M R, Chung Y G, Nolen L D, et al. Disruption of imprinted gene methylation and expression in cloned preimplantation stage mouse embryos. Biol Reprod. 2003; 69:902-914.
52. Bourc'his D, Le Bourhis D, Patin D, et al. Delayed and incomplete reprogramming of chromosome methylation patterns in bovine cloned embryos. Curr Biol. 2001; 11:1542-1546.
53. Kang Y K, Koo D B, Park J S, et al. Aberrant methylation of donor genome in cloned bovine embryos. Nat. Genet. 2001; 28:173-177.
54. Humphreys D, Eggan K, Akutsu H. et al. Abnormal gene expression in cloned mice derived from embryonic stem cell and cumulus cell nuclei. Proc Natl Acad Sci USA. 2002; 99:12889-12894.
55. Boiani M, Eckardt S, Scholer H R., Mclaughlin K J. Oct4 distribution and level in mouse clones: consequences for pluripotency. Genes Dev. 2002; 16:1209-1219.
56. Bortvin, A., Egan K, Skaletsky H, et al. Incomplete reactivation of Oct4-realted genes in mouse embryos cloned from somatic nuclei. Development. 2003; 130:1673-1680.
57. Boiani M, Echardt S, Leu N A, et al. Pluripotency deficit in clones overcome by clone-clone aggregation: epigenetic complementation? EMBO J. 2003; 22:5304-5312.
58. Cooney C A, Dave A A, Wolff G L. Maternal methyl supplements in mice affect epigenetic variation and DNA methylation of offspring. J. Nutr. 2002; 132:2393 S-2400S.
59. Choi S W, Mason J B. Folate Status: effects on pathways of colorectal carcinogenesis. J. Nutr. 2002; 132:2413 S-2418S.
60. Kim Y I. Folate and carcinogenesis: evidence, mechanisms, and implications. J Nutr Biochem. 1999; 10:66-88.
61. Lamprecht S A, Lipkin M. ChemopreVention of colon cancer by calcium, vitamin D and folate: molecular mechanisms. Nature Rev Cance. 2003; 3:601-614.

62. Kim Y I, Pgribny I P, Basnakian A G, et al. Folate deficiency in rats induces DNA strand breaks and hypomethylation within the p53 tumor suppressor gene. Am J Clin Nutr. 1997; 65:46-62,
63. Balaghi M, Warner C. DNA methylation in folate deficiency: use of CpG methylase. Bioch Biophys Res Commun. 1993; 193:1184-1190.
64. Ingrosso D, Cimmuno A, Perna A F, et al. Folate treatment and unbalanced methylation and changes in allelic expression induced by hyperhomocysteinaemia in patients with uranemia. Lancet. 2003; 361:1693-1699.
65. Cantoni G L, Chiang P K. The role of S-adenosylhomocysteine and S-adenosylhomocysteine hydrolase in the control of biological methylations. In: Natural Sulfur Compounds, pp 67-80, Plenum Press, New York, N.Y. 1980.
66. Kerr S J. Competing methyltransferase systems. J Biol. Chem. 1972; 247:4248-4252.
67. Wagner C, Briggs W T, Cook R J. Inhibition of glycine N-methyltransferase by folate derivatives: implications for regulation of methyl group metabolism. Bioch Biophys Res Comm. 1985; 127:746-752.
68. Wagner C, Decha-Umphai W, Corbin J. Phosphorylation modulates the activity of glycine N-methyltransferase, a folate binding protein. J Biol. Chem. 1989; 264:9638-9642.
69. Kutabach C, Stokstad E L R. Feedback inhibition of methylenetetrahydrofolate reductase. Biochem Biophys Acta. 1967; 250:459-477.
70. Jencks D A, Matthews R G. Allosteric inhibition of methylenetetrahydrofolate reductase by adenosylmethionine. J Biol. Chem. 1987; 262:2485-2493.
71. Rowling M J, Schalinske K L. Reinoid compounds activate and induce hepatic glycine N-methyltransferase in rats. J. Nut. 2001; 131:1914-1917.
72. McMullen M H, Rowling M J, Ozias M K, Schalinske K L. Activation and induction of glycine N-methyltransferase by retinoids are tissue- and gender specific. Arch Biochem Biphys. 2002; 401:73-80.
73. Rowling M J, McMullen M H, Schalinske K L. Vitamin A and its derivatives induce hepatic glycine N-methyltransferase and hypomethylation of DNA in rats. J. Nutr. 2002; 132:365-369.
74. RESERVED
75. RESERVED
76. Cezar G G, Bartolomei M S, Forsberg E J, First N L, Bishop M D, Eilertsen K J. Genome-wide epigenetic alterations in cloned bovine fetuses. Biol Reprod. 2003; 68:1009-1014.
77. RESERVED
78. RESERVED
79. RESERVED
80. RESERVED
81. RESERVED
82. J. Goffin and E. Eisenhauer Annals of Oncology 13:1699-1716, 2002
83. McKieman et al., Molecular Reproduction and Development 42:188-199, 1995
84. Sambrook et al., Molecular Cloning: A Laboratory Manual, Cold Spring Harbor, 2001
85. Miller & Calos, eds, Gene Transfer Vectors for Mammalian Cells, Cold Spring Harbor, 1987
86. F. M. Ausubel et al. eds., Current Protocols in Molecular Biology, Wiley & Sons,
87. J. E. Colligan et al. eds., Current Protocols in Protein Science, Wiley & Sons,
88. J. S. Bonifacino et al., Current Protocols in Cell Biology, Wiley & Sons,
89. J. E. Colligan et al. eds., Current protocols in Immunology, Wiley & Sons
90. R. I. Freshney ed., Culture of Animal Cells: A Manual of Basic Technique, Wiley & Sons, 2005
91. M. A. Harrison & I. F. Rae, General Techniques of Cell Culture, Cambridge Univ. Press
92. K. Turksen ed., Embryonic Stem Cells: Methods and Protocols, Humana Press, 2002
93. U.S. Pat. No. 5,635,387 to Fei, R., et al.
94. U.S. Pat. No. 5,460,964 to McGlave, et al.
95. U.S. Pat. No. 5,677,136 to Simmons, P., et al.
96. U.S. Pat. No. 5,750,397 to Tsukamoto, et al.
97. U.S. Pat. No. 759,793 to Schwartz, et al.
98. U.S. Pat. No. 5,681,599 to DiGuisto, et al.
99. U.S. Pat. No. 5,716,827 to Tsukamoto, et al.
100. Hill, B., et al., Exp. Hematol. (1996) 24 (8): 936 943).
101. Gage F H:Science 287:1433 1438, 2000
102. Svendsen C N et al, Brain Path 9:499 513, 1999
103. Okabe S et al, Mech Dev 59:89 102, 1996)
104. Fridenshtein, Arkh. Patol, 44:3 11, 1982
105. U.S. Pat. No. 5,486,359 to Caplan, A., et al.
106. U.S. Pat. No. 5,827,735 to Young, H., et al.
107. U.S. Pat. No. 5,811,094 to Caplan, A., et al.
108. U.S. Pat. No. 5,736,396 to Bruder, S., et al.
109. U.S. Pat. No. 5,837,539 to Caplan, A., et al.
110. U.S. Pat. No. 5,837,670 to Masinovsky, B.
111. U.S. Pat. No. 5,827,740 to Pittenger, M.
112. Jaiswal, N., et al., J. Cell Biochem. (1997) 64(2): 295 312
113. Cassiede P., et al., J. Bone Miner. Res. (1996) 11(9): 1264 1273;
114. Johnstone, B., et al., Exp. Cell Res. (1998) 238(1): 265 272
115. Yoo, et al., J. Bone Joint Sure. Am. (1998) 80(12): 1745 1757
116. Gronthos, S., Blood (1994) 84(12): 416-44173
117. Makin, S., et al., J. Clin. Invest. (1999) 103(5): 697 705).
118. Pittenger, et al., Science (1999) 284: 143 147
119. Potten C, Philos Trans R Soc Lond B Biol Sci 353:821 30, 1998
120. Watt F, Philos. Trans R Soc Lond B Biol Sci 353:831, 1997
121. Alison M et al, Hepatol 29:678 83, 1998)
122. Ferrari, Science 279:528 30, 1998
123. Gussoni Nature 401:390 4, 1999
124. Jackson PNAS USA 96:14482 6, 1999
125. Takahashi, Nat Med 5:434 8, 1999
126. Lin, Clin Invest 105:71 7, 2000
127. Petersen, Science 284:1168 1170, 1999
128. Theise, Hepatology 31:235 40, 2000
129. Theise, Hepatology 32:11 6, 2000
130. Clarke, Science 288:1660 3, 2000
131. Forsberg, et al. Biol. Reprod. 2002 67:327-333
132. Wadman, M., Nature (1999) 398: 551
133. Leu et al., Cancer Res. (2003) 63:6110-6115
134. Stresemann et al., Cancer Res. (2006) 66:2794-2800
135. Detich et al., J. Biol. Chem. (2003) 278:27586-27592
136. Blelloch, R, et al., Stem Cells, 2006 in press, Epub ahead of print May 18
137. Chung Y G, et al, Biol Reprod, 2002 April; 66(4):1178-84
138. Cowan C A, et al., Science, 2005 Sep. 9; 122(5):653-4.
139. Gao S, et al., Biol Reprod, 2003 July; 69(1):48-56.
140. Robert et al. (Nat. Genet. 2003 33:61-65)

What is claimed is:

1. A method for identifying compounds that affect cell differentiation comprising:
   (a) contacting a cell having a first phenotype with a compound, wherein the compound reduces the percentage of cytosines in DNA of a cell that are methylated and upregulates the gene encoding glycine-N-methyltransferase (GNMT); and
   (b) comparing the first phenotype of the cell to a phenotype obtained after step (a), wherein an appearance of a phenotype after step (a) that is characteristic of cell differentiation indicates that the compound has an effect on cell differentiation.

2. The method of claim 1, wherein step (a) comprises reducing the percentage of cytosines in the DNA of the cell that are methylated by at least about 5%.

3. The method of claim 1, wherein step (a) comprises reducing the percentage of cytosines in the DNA of the cell that are methylated by at least about 10%.

4. The method of claim 1, wherein the cell includes a reporter system to monitor changes in transcription.

5. The method of claim 4, wherein the reporter system measures presence of an enzyme activity selected from the group consisting of luciferase activity, beta-lactamase activity, and beta-galactosidase activity.

6. The method of claim 1, wherein step (a) comprises reducing the percentage of cytosines in the DNA of the cell that are methylated by at least about 15%.

7. The method of claim 1, wherein step (a) comprises reducing the percentage of cytosines in the DNA of the cell that are methylated by at least about 20%.

8. The method of claim 1, wherein step (a) comprises reducing the percentage of cytosines in the DNA of the cell that are methylated by at least about 25%.

9. The method of claim 1, wherein the compound is retinoic acid.

* * * * *